(12) United States Patent
Gajewiak et al.

(10) Patent No.: US 10,947,274 B1
(45) Date of Patent: Mar. 16, 2021

(54) SYNTHETIC ANALGESIC PEPTIDES OF RGIA ANALOGS

(71) Applicant: University of Utah Research Foundation, Salt Lake City, UT (US)

(72) Inventors: Joanna Gajewiak, Salt Lake City, UT (US); J. Michael McIntosh, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/391,044

(22) Filed: Apr. 22, 2019

Related U.S. Application Data

(60) Provisional application No. 62/665,006, filed on May 1, 2018, provisional application No. 62/729,753, filed on Sep. 11, 2018.

(51) Int. Cl.

| | | |
|---|---|---|
| *C07K 7/08* | (2006.01) | |
| *C07K 7/00* | (2006.01) | |
| *A61K 38/00* | (2006.01) | |
| *A61K 38/10* | (2006.01) | |
| *A61P 25/02* | (2006.01) | |
| *A61P 29/02* | (2006.01) | |
| *A61P 25/00* | (2006.01) | |
| *A61P 25/04* | (2006.01) | |
| *A61P 29/00* | (2006.01) | |

(52) U.S. Cl.
CPC ............ *C07K 7/08* (2013.01); *A61K 38/10* (2013.01); *A61P 25/00* (2018.01); *A61P 25/02* (2018.01); *A61P 25/04* (2018.01); *A61P 29/00* (2018.01); *A61P 29/02* (2018.01); *A61K 38/00* (2013.01)

(58) Field of Classification Search
CPC .... A61K 2300/00; A61K 38/10; A61K 38/17; A61K 38/1709; A61K 8/64; A61K 31/664; A61K 38/12; A61K 38/16; C07K 7/08; C07K 1/006; C07K 14/00; A61P 29/00; A61P 25/00; A61P 43/00; A61P 25/04; A61P 25/28; G01N 33/68
See application file for complete search history.

(56) References Cited

U.S. PATENT DOCUMENTS

| 10,633,417 B2 * | 4/2020 | McIntosh | A61P 17/00 |
| 2016/0122388 A1 * | 5/2016 | McIntosh | A61P 31/04 514/18.3 |
| 2018/0362599 A1 * | 12/2018 | Posakony | A61K 47/542 |

FOREIGN PATENT DOCUMENTS

| WO | WO2014194284 | * 12/2014 |

OTHER PUBLICATIONS

Chhabra et al., J. Med. Chem. 2014; 57:9933-9944.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Zheng et al.,J. Ann. Chem. Soc. 2015, 137:15094-15097.*

* cited by examiner

*Primary Examiner* — Chang-Yu Wang
(74) *Attorney, Agent, or Firm* — Michael Best & Friedrich LLP

(57) ABSTRACT

The present invention relates to synthetic analgesic peptides that are analogs of the α-conotoxin peptide RgIA and their use for treating pain and other disorders.

2 Claims, 2 Drawing Sheets

Specification includes a Sequence Listing.

SEQUENCE LISTING

<160> NUMBER OF SEQ ID NOS: 41

<210> SEQ ID NO 1
<211> LENGTH: 13
<212> TYPE: PRT
<213> ORGANISM: Conus regius

<400> SEQUENCE: 1

Gly Cys Cys Ser Asp Pro Arg Cys Arg Tyr Arg Cys Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(3)
<223> OTHER INFORMATION: L-Penicillamine or D-Penicillamine or
      L-Cysteine
<220> FEATURE:
<221> NAME/KEY: MISC_FEATURE
<222> LOCATION: (8)..(8)
<223> OTHER INFORMATION: L-Penicillamine or D-Penicillamine or
      L-Cysteine
<220> FEATURE:
<221> NAME/KEY: MISC_FEATURE
<222> LOCATION: (9)..(9)
<223> OTHER INFORMATION: Citrulline or Arginine
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine or
      L-Cysteine
<220> FEATURE:
<221> NAME/KEY: MISC_FEATURE
<222> LOCATION: (13)..(13)
<223> OTHER INFORMATION: L-Tyrosine or D-Tyrosine
<220> FEATURE:
<221> NAME/KEY: MISC_FEATURE
<222> LOCATION: (14)..(14)
<223> OTHER INFORMATION: any amino acid

<400> SEQUENCE: 2

Gly Xaa Xaa Thr Asp Pro Arg Xaa Xaa Xaa Gln Xaa Xaa Xaa
1               5                   10

<210> SEQ ID NO 3
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine or
      L-Cysteine
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (8)..(8)
<223> OTHER INFORMATION: L-Penicillamine or D-Penicillamine or
      L-Cysteine
<220> FEATURE:

```
<221> NAME/KEY: MISC_FEATURE
<222> LOCATION: (9)..(9)
<223> OTHER INFORMATION: Citrulline or Arginine
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine or
      L-Cysteine
<220> FEATURE:
<221> NAME/KEY: MISC_FEATURE
<222> LOCATION: (13)..(13)
<223> OTHER INFORMATION: L-Tyrosine or D-Tyrosine
<220> FEATURE:
<221> NAME/KEY: MISC_FEATURE
<222> LOCATION: (14)..(14)
<223> OTHER INFORMATION: any amino acid

<400> SEQUENCE: 3

Gly Xaa Xaa Thr Asp Pro Arg Xaa Xaa Xaa Gln Xaa Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine or
      L-Cysteine
<220> FEATURE:
<221> NAME/KEY: MISC_FEATURE
<222> LOCATION: (3)..(3)
<223> OTHER INFORMATION: D-Penicillamine
<220> FEATURE:
<221> NAME/KEY: MISC_FEATURE
<222> LOCATION: (8)..(8)
<223> OTHER INFORMATION: L-Penicillamine or D-Penicillamine or
      L-Cysteine
<220> FEATURE:
<221> NAME/KEY: MISC_FEATURE
<222> LOCATION: (9)..(9)
<223> OTHER INFORMATION: Citrulline or Arginine
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine or
      L-Cysteine
<220> FEATURE:
<221> NAME/KEY: MISC_FEATURE
<222> LOCATION: (13)..(13)
<223> OTHER INFORMATION: L-Tyrosine or D-Tyrosine
<220> FEATURE:
<221> NAME/KEY: MISC_FEATURE
<222> LOCATION: (14)..(14)
<223> OTHER INFORMATION: any amino acid

<400> SEQUENCE: 4

Gly Xaa Xaa Thr Asp Pro Arg Xaa Xaa Xaa Gln Xaa Xaa Xaa
1               5                   10

<210> SEQ ID NO 5
<211> LENGTH: 13
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine

<400> SEQUENCE: 5

Gly Xaa Cys Thr Asp Pro Arg Cys Xaa Xaa Gln Cys Tyr
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine

<400> SEQUENCE: 6

Gly Cys Xaa Thr Asp Pro Arg Cys Xaa Xaa Gln Cys Tyr
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: L-Penicillamine or D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine

<400> SEQUENCE: 7

Gly Cys Cys Thr Asp Pro Arg Xaa Xaa Xaa Gln Cys Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine

<400> SEQUENCE: 8

Gly Cys Cys Thr Asp Pro Arg Cys Xaa Xaa Gln Xaa Tyr
1               5                  10

<210> SEQ ID NO 9
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine or
      L-Cysteine
<220> FEATURE:
<221> NAME/KEY: MISC_FEATURE
<222> LOCATION: (8)..(8)
<223> OTHER INFORMATION: L-Penicillamine or D-Penicillamine or
      L-Cysteine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine

<400> SEQUENCE: 9

Gly Xaa Cys Thr Asp Pro Arg Xaa Xaa Xaa Gln Cys Tyr
1               5                  10

<210> SEQ ID NO 10
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine or
      L-Cysteine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine or
      L-Cysteine

<400> SEQUENCE: 10

Gly Cys Xaa Thr Asp Pro Arg Cys Xaa Xaa Gln Xaa Tyr
1               5                  10
```

-continued

<210> SEQ ID NO 11
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (13)..(13)
<223> OTHER INFORMATION: L-Tyrosine or D-Tyrosine
<220> FEATURE:
<221> NAME/KEY: MISC_FEATURE
<222> LOCATION: (14)..(14)
<223> OTHER INFORMATION: any amino acid

<400> SEQUENCE: 11

Gly Cys Xaa Thr Asp Pro Arg Cys Xaa Xaa Gln Cys Xaa Xaa
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine
<220> FEATURE:
<221> NAME/KEY: MISC_FEATURE
<222> LOCATION: (10)..(10)
<223> OTHER INFORMATION: 3-R-tyrosine

<400> SEQUENCE: 12

Gly Xaa Cys Thr Asp Pro Arg Cys Arg Xaa Gln Cys Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine
<220> FEATURE:
<221> NAME/KEY: MISC_FEATURE
<222> LOCATION: (10)..(10)
<223> OTHER INFORMATION: 3-R-tyrosine

<400> SEQUENCE: 13

Gly Cys Xaa Thr Asp Pro Arg Cys Arg Xaa Gln Cys Tyr
1               5                   10

<210> SEQ ID NO 14
<211> LENGTH: 13
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: L-Penicillamine or D-Penicillamine
<220> FEATURE:
<221> NAME/KEY: MISC_FEATURE
<222> LOCATION: (10)..(10)
<223> OTHER INFORMATION: 3-R-tyrosine

<400> SEQUENCE: 14

Gly Cys Cys Thr Asp Pro Arg Xaa Arg Xaa Gln Cys Tyr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine

<400> SEQUENCE: 15

Gly Cys Cys Thr Asp Pro Arg Cys Arg Xaa Gln Xaa Tyr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine or D-Penicillamine or
      L-Cysteine
<220> FEATURE:
<221> NAME/KEY: MISC_FEATURE
<222> LOCATION: (8)..(8)
<223> OTHER INFORMATION: L-Penicillamine or D-Penicillamine or
      L-Cysteine
<220> FEATURE:
<221> NAME/KEY: MISC_FEATURE
<222> LOCATION: (10)..(10)
<223> OTHER INFORMATION: 3-R-tyrosine

<400> SEQUENCE: 16

Gly Xaa Cys Thr Asp Pro Arg Xaa Arg Xaa Gln Cys Tyr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine or
      L-Cysteine
<220> FEATURE:
<221> NAME/KEY: MISC_FEATURE
<222> LOCATION: (10)..(10)
```

```
<223> OTHER INFORMATION: 3-R-tyrosine
<220> FEATURE:
<221> NAME/KEY: MISC_FEATURE
<222> LOCATION: (12)..(12)
<223> OTHER INFORMATION: L-Penicillamine or D-Penicillamine or
      L-Cysteine

<400> SEQUENCE: 17

Gly Cys Xaa Thr Asp Pro Arg Cys Arg Xaa Gln Xaa Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine or D-Penicillamine
<220> FEATURE:
<221> NAME/KEY: MISC_FEATURE
<222> LOCATION: (10)..(10)
<223> OTHER INFORMATION: 3-R-tyrosine
<220> FEATURE:
<221> NAME/KEY: MISC_FEATURE
<222> LOCATION: (13)..(13)
<223> OTHER INFORMATION: L-Tyrosine or D-Tyrosine
<220> FEATURE:
<221> NAME/KEY: MISC_FEATURE
<222> LOCATION: (14)..(14)
<223> OTHER INFORMATION: any amino acid

<400> SEQUENCE: 18

Gly Cys Xaa Thr Asp Pro Arg Cys Arg Xaa Gln Cys Xaa Xaa
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: pyroglutamate or des-Xaa
<220> FEATURE:
<221> NAME/KEY: MISC_FEATURE
<222> LOCATION: (2)..(2)
<223> OTHER INFORMATION: L-Glycine or des-Xaa or pyroglutamate
<220> FEATURE:
<221> NAME/KEY: MISC_FEATURE
<222> LOCATION: (3)..(3)
<223> OTHER INFORMATION: L-Cysteine or L-Penicillamine or
      D-Penicillamine
<220> FEATURE:
<221> NAME/KEY: MISC_FEATURE
<222> LOCATION: (4)..(4)
<223> OTHER INFORMATION: L-Penicillamine or D-Penicillamine
<220> FEATURE:
<221> NAME/KEY: MISC_FEATURE
<222> LOCATION: (8)..(8)
<223> OTHER INFORMATION: the Third Group of Peptide Residues
<220> FEATURE:
<221> NAME/KEY: MISC_FEATURE
<222> LOCATION: (10)..(10)
<223> OTHER INFORMATION: Citrulline
<220> FEATURE:
<221> NAME/KEY: MISC_FEATURE
<222> LOCATION: (11)..(11)
<223> OTHER INFORMATION: the First Group of Peptide Residues
<220> FEATURE:
<221> NAME/KEY: MISC_FEATURE
```

```
<222> LOCATION: (12)..(12)
<223> OTHER INFORMATION: - L-Glutamine or D-Glutamine or L-Asparagine or
      D-Asparagine or the Third Group of Peptide Residues
<220> FEATURE:
<221> NAME/KEY: MISC_FEATURE
<222> LOCATION: (14)..(14)
<223> OTHER INFORMATION: L-Tyrosine or D-Tyrosine or D-beta homo amino
      acid or L-beta homo amino acid or the Second Group of Peptide
      Residues or the Third Group of Peptide Residues

<400> SEQUENCE: 19

Xaa Xaa Xaa Xaa Thr Asp Pro Xaa Cys Xaa Xaa Xaa Cys Xaa
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: pyroglutamate or des-Xaa
<220> FEATURE:
<221> NAME/KEY: MISC_FEATURE
<222> LOCATION: (2)..(2)
<223> OTHER INFORMATION: L-Glycine or des-Xaa or pyroglutamate
<220> FEATURE:
<221> NAME/KEY: MISC_FEATURE
<222> LOCATION: (3)..(3)
<223> OTHER INFORMATION: L-Cysteine or L-Penicillamine or
      D-Penicillamine
<220> FEATURE:
<221> NAME/KEY: MISC_FEATURE
<222> LOCATION: (4)..(4)
<223> OTHER INFORMATION: L-Penicillamine or D-Penicillamine
<220> FEATURE:
<221> NAME/KEY: MISC_FEATURE
<222> LOCATION: (8)..(8)
<223> OTHER INFORMATION: the Third Group of Peptide Residues
<220> FEATURE:
<221> NAME/KEY: MISC_FEATURE
<222> LOCATION: (10)..(10)
<223> OTHER INFORMATION: the Third Group of Peptide Residues
<220> FEATURE:
<221> NAME/KEY: MISC_FEATURE
<222> LOCATION: (11)..(11)
<223> OTHER INFORMATION: the First Group of Peptide Residues
<220> FEATURE:
<221> NAME/KEY: MISC_FEATURE
<222> LOCATION: (12)..(12)
<223> OTHER INFORMATION: L-Glutamine or D-Glutamine or L-Asparagine or
      D-Asparagine or the Third Group of Peptide Residues
<220> FEATURE:
<221> NAME/KEY: MISC_FEATURE
<222> LOCATION: (14)..(14)
<223> OTHER INFORMATION: L-Tyrosine or D-Tyrosine or D-beta homo amino
      acid or L-beta homo amino acid or the Second Group of Peptide
      Residues or the Third Group of Peptide Residues

<400> SEQUENCE: 20

Xaa Xaa Xaa Xaa Thr Asp Pro Xaa Cys Xaa Xaa Xaa Cys Xaa
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: pyroglutamate or des-Xaa
```

```
<220> FEATURE:
<221> NAME/KEY: MISC_FEATURE
<222> LOCATION: (2)..(2)
<223> OTHER INFORMATION: L-Glycine or des-Xaa or pyroglutamate
<220> FEATURE:
<221> NAME/KEY: MISC_FEATURE
<222> LOCATION: (3)..(3)
<223> OTHER INFORMATION: L-Cysteine or L-Penicillamine or
      D-Penicillamine
<220> FEATURE:
<221> NAME/KEY: MISC_FEATURE
<222> LOCATION: (4)..(4)
<223> OTHER INFORMATION: L-Penicillamine or D-Penicillamine
<220> FEATURE:
<221> NAME/KEY: MISC_FEATURE
<222> LOCATION: (8)..(8)
<223> OTHER INFORMATION: the Third Group of Peptide Residues
<220> FEATURE:
<221> NAME/KEY: MISC_FEATURE
<222> LOCATION: (10)..(10)
<223> OTHER INFORMATION: Citrulline
<220> FEATURE:
<221> NAME/KEY: MISC_FEATURE
<222> LOCATION: (11)..(11)
<223> OTHER INFORMATION: the First Group of Peptide Residues
<220> FEATURE:
<221> NAME/KEY: MISC_FEATURE
<222> LOCATION: (12)..(12)
<223> OTHER INFORMATION: L-Glutamine or D-Glutamine or L-Asparagine or
      D-Asparagine or the Third Group of Peptide Residues
<220> FEATURE:
<221> NAME/KEY: MISC_FEATURE
<222> LOCATION: (14)..(14)
<223> OTHER INFORMATION: L-Tyrosine or D-Tyrosine or D-beta homo amino
      acid or L-beta homo amino acid or the Second Group of Peptide
      Residues or the Third Group of Peptide Residues
<220> FEATURE:
<221> NAME/KEY: MISC_FEATURE
<222> LOCATION: (15)..(15)
<223> OTHER INFORMATION: L-amino acid or D-amino acid or L-beta homo
      amino acid or D-beta amino acid or the Second Group of Peptide
      Residues or the Third Group of Peptide Residues

<400> SEQUENCE: 21

Xaa Xaa Xaa Xaa Thr Asp Pro Xaa Cys Xaa Xaa Xaa Cys Xaa Xaa
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: pyroglutamate or des-Xaa
<220> FEATURE:
<221> NAME/KEY: MISC_FEATURE
<222> LOCATION: (2)..(2)
<223> OTHER INFORMATION: L-Glycine or des-Xaa or pyroglutamate
<220> FEATURE:
<221> NAME/KEY: MISC_FEATURE
<222> LOCATION: (3)..(3)
<223> OTHER INFORMATION: L-Cysteine or L-Penicillamine or
      D-Penicillamine
<220> FEATURE:
<221> NAME/KEY: MISC_FEATURE
<222> LOCATION: (4)..(4)
<223> OTHER INFORMATION: L-Penicillamine or D-Penicillamine
<220> FEATURE:
<221> NAME/KEY: MISC_FEATURE
<222> LOCATION: (8)..(8)
<223> OTHER INFORMATION: the Third Group of Peptide Residues
<220> FEATURE:
<221> NAME/KEY: MISC_FEATURE
<222> LOCATION: (10)..(10)
```

```
<223> OTHER INFORMATION: the Third Group of Peptide Residues
<220> FEATURE:
<221> NAME/KEY: MISC_FEATURE
<222> LOCATION: (11)..(11)
<223> OTHER INFORMATION: the First Group of Peptide Residues
<220> FEATURE:
<221> NAME/KEY: MISC_FEATURE
<222> LOCATION: (12)..(12)
<223> OTHER INFORMATION: L-Glutamine or D-Glutamine or L-Asparagine or
      D-Asparagine or the Third Group of Peptide Residues
<220> FEATURE:
<221> NAME/KEY: MISC_FEATURE
<222> LOCATION: (14)..(14)
<223> OTHER INFORMATION: L-Tyrosine or D-Tyrosine or D-beta homo amino
      acid or L-beta homo amino acid or the Second Group of Peptide
      Residues or the Third Group of Peptide Residues
<220> FEATURE:
<221> NAME/KEY: MISC_FEATURE
<222> LOCATION: (15)..(15)
<223> OTHER INFORMATION: L-amino acid or D-amino acid or L-beta homo
      amino acid or D-beta amino acid or the Second Group of Peptide
      Residues or the Third Group of Peptide Residues

<400> SEQUENCE: 22

Xaa Xaa Xaa Xaa Thr Asp Pro Xaa Cys Xaa Xaa Xaa Cys Xaa Xaa
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 23

Gly Xaa Cys Thr Asp Pro Arg Cys Xaa Xaa Gln Cys Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 24

Gly Cys Xaa Thr Asp Pro Arg Cys Xaa Xaa Gln Cys Tyr
1               5                   10
```

-continued

```
<210> SEQ ID NO 25
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 25

Gly Cys Cys Thr Asp Pro Arg Xaa Xaa Xaa Gln Cys Tyr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (12)..(12)
<223> OTHER INFORMATION: L-Penicillamine

<400> SEQUENCE: 26

Gly Cys Cys Thr Asp Pro Arg Cys Xaa Xaa Gln Xaa Tyr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-Penicillamine
<220> FEATURE:
<221> NAME/KEY: MISC_FEATURE
<222> LOCATION: (8)..(8)
<223> OTHER INFORMATION: L-Penacillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 27

Gly Xaa Cys Thr Asp Pro Arg Xaa Xaa Xaa Gln Cys Tyr
1               5                   10
```

```
<210> SEQ ID NO 28
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (12)..(12)
<223> OTHER INFORMATION: L-Penacillamine

<400> SEQUENCE: 28

Gly Cys Xaa Thr Asp Pro Arg Cys Xaa Xaa Gln Xaa Tyr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 29

Gly Xaa Cys Thr Asp Pro Arg Cys Xaa Xaa Gln Cys Tyr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: D-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 30

Gly Cys Xaa Thr Asp Pro Arg Cys Xaa Xaa Gln Cys Tyr
1               5                   10
```

```
<210> SEQ ID NO 31
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (12)..(12)
<223> OTHER INFORMATION: D-Penicillamine

<400> SEQUENCE: 31

Gly Cys Cys Thr Asp Pro Arg Cys Xaa Xaa Gln Xaa Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: D-tyrosine

<400> SEQUENCE: 32

Gly Cys Xaa Thr Asp Pro Arg Cys Xaa Xaa Gln Cys Xaa
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: D-tyrosine
<220> FEATURE:
<221> NAME/KEY: MISC_FEATURE
<222> LOCATION: (14)..(14)
```

```
<223> OTHER INFORMATION: D-arginine

<400> SEQUENCE: 33

Gly Cys Xaa Thr Asp Pro Arg Cys Xaa Xaa Gln Cys Xaa Xaa
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 34

Gly Cys Xaa Thr Asp Pro Arg Cys Xaa Xaa Gln Cys Tyr Arg
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: beta-homotyrosine

<400> SEQUENCE: 35

Gly Cys Xaa Thr Asp Pro Arg Cys Xaa Xaa Gln Cys Xaa Arg
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
```

```
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: beta-homotyrosine
<220> FEATURE:
<221> NAME/KEY: MISC_FEATURE
<222> LOCATION: (14)..(14)
<223> OTHER INFORMATION: D-arginine

<400> SEQUENCE: 36

Gly Cys Xaa Thr Asp Pro Arg Cys Arg Xaa Gln Cys Xaa Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: beta-homotyrosine

<400> SEQUENCE: 37

Gly Cys Xaa Thr Asp Pro Arg Cys Arg Xaa Gln Cys Xaa Arg
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (10)..(10)
<223> OTHER INFORMATION: 3-Iodo-tyrosine
<220> FEATURE:
<221> NAME/KEY: MISC_FEATURE
<222> LOCATION: (13)..(13)
<223> OTHER INFORMATION: beta-homotyrosine
<220> FEATURE:
<221> NAME/KEY: MISC_FEATURE
<222> LOCATION: (14)..(14)
<223> OTHER INFORMATION: D-arginine

<400> SEQUENCE: 38

Gly Cys Xaa Thr Asp Pro Arg Cys Arg Xaa Gln Cys Xaa Xaa
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
```

```
<223> OTHER INFORMATION: Citrulline
<220> FEATURE:
<221> NAME/KEY: MISC_FEATURE
<222> LOCATION: (10)..(10)
<223> OTHER INFORMATION: 3-Iodo-tyrosine

<400> SEQUENCE: 39

Gly Cys Cys Thr Asp Pro Arg Cys Xaa Xaa Gln Cys Tyr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: 3-Iodo-tyrosine

<400> SEQUENCE: 40

Gly Cys Cys Thr Asp Pro Arg Cys Arg Xaa Gln Cys Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-Penicillamine
<220> FEATURE:
<221> NAME/KEY: MISC_FEATURE
<222> LOCATION: (10)..(10)
<223> OTHER INFORMATION: 3-Iodo-tyrosine

<400> SEQUENCE: 41

Gly Cys Xaa Thr Asp Pro Arg Cys Arg Xaa Gln Cys Tyr Arg
1               5                   10
```

SYNTHETIC ANALGESIC PEPTIDES OF RGIA ANALOGS

CROSS-REFERENCE TO RELATED APPLICATIONS

This application claims priority to U.S. Provisional Application No. 62/729,753, filed Sep. 11, 2018, and to U.S. Provisional Application No. 62/665,006, filed May 1, 2018, each of which is incorporated by reference herein in its entirety.

REFERENCE TO GOVERNMENT SUPPORT

This invention was made with government support under grant numbers P01 GM048677 and R01 GM103801 awarded by National Institutes of Health. The government has certain rights in the invention.

TECHNICAL FIELD

The present invention relates to synthetic analgesic peptides and their use for treatment of pain.

BACKGROUND OF THE INVENTION

The present invention relates to synthetic analgesic peptides that are analogs of the α-conotoxin peptide RgIA. These synthetic analgesic peptides block the α9α10 subtype of the nicotinic acetylcholine receptor (nAChR) and can be used for treating pain, such as neuropathic pain, for example, diabetic peripheral neuropathic pain, and chemotherapy-induced peripheral neuropathy, inflammatory pain, inflammatory disorders, such as rheumatic diseases, post-surgical pain, migraines, and for the treatment of breast cancer.

nAChRs are a group of acetylcholine gated ion channels that are part of the ligand gated ion channel superfamily (Karlin, 2002; Gotti and Clementi, 2004). They are pentamers of transmembrane subunits surrounding a central ion conducting channel. Many different subunits have been identified, and most fall into two main subfamilies (the α subunits and the β subunits). The subunits can associate in various combinations in the receptor pentamers, leading to a diverse family of receptor subtypes. Most of the subtypes contain subunits from both the α and β subunit families, e.g., the human adult muscle subtype contains two α1 subunits and a β1 subunit (in addition to a δ and an ε subunit) and the α3β2 subtype is composed of α3 and β2 subunits. nAChRs that are composed of only α subunits are the α7 and α9 subtypes (homopentamers) and the α9α10 subtype (an all α heteropentamer). Phylogenetic analysis shows that the α7, α9, and α10 subunits are more closely related to each other than they are to other nAChR subunits (Le Novere et al., 2002; Sgard et al., 2002).

The α9 and α10 nAChR subunits are expressed in diverse tissues. In the inner ear α9α10 nAChRs mediate synaptic transmission between efferent olivocochlear fibers and cochlear hair cells (Sgard et al., 2002; Elgoyhen et al., 1994; Elgoyhen et al., 2001). The α9 and α10 subunits are also found in dorsal root ganglion neurons (Harberger et al., 2004; Lips et al., 2002), lymphocytes (Peng et al., 2004), skin keratinocytes (Arredondo et al., 2002; Nguyen et al., 2000; Kurzen et al., 2004), and the pars tuberalis of the pituitary (Sgard et al., 2002; Elgoyhen et al., 1994; Elgoyhen et al., 2001). In addition, the α9 nAChR subunit is known to be active in breast cancer (Lee et al., 2010a; Lee et al. 2010b; Linnoila, 2010). Thus, antagonists of the α9 nAChR subunit would be expected to be useful in the treatment of breast cancer. α-Conotoxin RgIA (GCCSDPRCRYRCR; SEQ ID NO: 1) has been shown to block α9α10 nAChR (Ellison et al., 2006).

Opioids are first line drugs for moderate to severe acute pain which has contributed to an opioid overdose epidemic being a critical public health crisis. There is therefore a demand for more active, non-opioid analgesic agents with diminished side effects and toxicity, and which are non-addictive.

SUMMARY OF THE INVENTION

The invention provides for synthetic analgesic peptides comprising the amino acid sequence G X1 X1 T D P R X1 (Cit)/R (R-3-Y) Q X1 X2 X3 (SEQ ID NO: 2), wherein, with respect to each of the sequences in the set of sequences having SEQ ID NO: 2 through SEQ ID NO: 4, the following selection conditions are applied independently across the set of sequences:

X1 in at least one occurrence thereof, and up to and including all occurrences thereof, is in each position independently selected from the group consisting of L-Penicillamine (L-Pen) and D-Penicillamine (D-Pen), and in all other occurrences thereof, if any, is L-Cysteine;

X2 is selected from the group consisting of L-Tyrosine and D-Tyrosine;

X3 is any amino acid,

Cit is citrulline, and

R-3-Y is 3-R-tyrosine.

In another embodiment, X3 is selected from the group consisting of L-Arginine and D-Arginine.

In another embodiment, the synthetic analgesic peptide comprises the amino acid sequence G X1 L-Pen T D P R X1 (Cit)/R (R-3-Y) Q X1 X2 X3 (SEQ ID NO: 3).

In another embodiment, the synthetic analgesic peptide comprises the amino acid sequence G X1 D-Pen T D P R X1 (Cit)/R (R-3-Y) Q X1 X2 X3 (SEQ ID NO: 4).

In another embodiment, the C-terminal amino acid of the synthetic analgesic peptide is amidated.

The invention also provides for a synthetic analgesic peptide comprising an amino acid sequence selected from the group consisting of:

a. G X1 C T D P R C (Cit) (R-3-Y) Q C Y (SEQ ID NO: 5);
b. G C X1 T D P R C (Cit) (R-3-Y) Q C Y (SEQ ID NO: 6);
c. G C C T D P R X1 (Cit) (R-3-Y) Q C Y (SEQ ID NO: 7);
d. G C C T D P R C (Cit) (R-3-Y) Q X1 Y (SEQ ID NO: 8);
e. G X1 C T D P R X1 (Cit) (R-3-Y) Q C Y (SEQ ID NO: 9);
f. G C X1 T D P R C (Cit) (R-3-Y) Q X1 Y (SEQ ID NO: 10);
g. G C X1 T D P R C (Cit) (R-3-Y) Q C X2 X3 (SEQ ID NO: 11);
h. G X1 C T D P R C R (R-3-Y) Q C Y (SEQ ID NO: 12);
i. G C X1 T D P R C R (R-3-Y) Q C Y (SEQ ID NO: 13);
j. G C C T D P R X1 R (R-3-Y) Q C Y (SEQ ID NO: 14);
k. G C C T D P R C R (R-3-Y) Q X1 Y (SEQ ID NO: 15);
l. G X1 C T D P R X1 R (R-3-Y) Q C Y (SEQ ID NO: 16);
m. G C X1 T D P R C R (R-3-Y) Q X1 Y (SEQ ID NO:17); and
n. G C X1 T D P R C R (R-3-Y) Q C X2 X3 (SEQ ID NO: 18);

wherein, with respect to each of the foregoing sequences in the set of sequences having SEQ ID NO: 5 through SEQ ID NO: 18, the following selection conditions are applied independently across the set of sequences:

X1 in at least one occurrence thereof in such sequence, and up to and including all occurrences thereof in such sequence, is in each position independently selected from the group consisting of L-Penicillamine (L-Pen) and D-Penicillamine (D-Pen), and in all other occurrences thereof, if any, is L-Cysteine;

X2 in such sequence is selected from the group consisting of L-Tyrosine and D-Tyrosine;

X3 in such sequence is any amino acid,

Cit is citrulline, and

R-3-Y is 3-R-tyrosine.

In one embodiment, X3 is selected from the group consisting of L-Arginine and D-Arginine.

In another embodiment, the C-terminal amino acid of the synthetic analgesic peptide is amidated.

The invention also provides for a synthetic analgesic peptide comprising an amino acid sequence selected from the group consisting of:

a. X0 X1 X2 X3 T D P X4 C (Cit) X5 X6 C X7 (SEQ ID NO: 19);

b. X0 X1 X2 X3 T D P X4 C X4 X5 X6 C X7 (SEQ ID NO: 20);

c. X0 X1 X2 X3 T D P X4 C (Cit) X5 X6 C X7 X8 (SEQ ID NO: 21); and d. X0 X1 X2 X3 T D P X4 C X4 X5 X6 C X7 X8 (SEQ ID NO: 22);

wherein, with respect to each of the foregoing sequences in the set of sequences having SEQ ID NO: 19 through SEQ ID NO: 22, the following selection conditions are applied independently across the set of sequences:

X0 in such sequence is pyroglutamate or des-X0;

X1 in such sequence is selected from the group consisting of L-Glycine, des-X1, and pyroglutamate;

X2 in such sequence is selected from the group consisting of L-Cysteine, L-Penicillamine and D-Penicillamine;

X3 in such sequence is selected from the group consisting of L-Penicillamine and D-Penicillamine;

X4 in such sequence is, in each position, independently selected from the group consisting of the Third Group of Peptide Residues;

X5 in such sequence is selected from the group consisting of the First Group of Peptide Residues;

X6 in such sequence is selected from the group consisting of L-Glutamine, D-Glutamine, L-Asparagine, D-Asparagine, and the Third Group of Peptide Residues;

X7 in such sequence is selected from the group consisting of L-Tyrosine, D-Tyrosine, a D-beta homo amino acid, an L-beta homo amino acid, the Second Group of Peptide Residues, and the Third Group of Peptide Residues;

X8 in such sequence is selected from the group consisting of an L-amino acid, a D-amino acid, an L-beta homo amino acid, a D-beta homo amino acid, the Second Group of Peptide Residues, and the Third Group of Peptide Residues;

Cit is citrulline; and in the synthetic analgesic peptide, the C-terminal amino acid is selected from the group consisting of amidated amino acids and non-amidated amino acids.

The invention also provides for a method for treating or preventing a condition or disorder associate with α9α10 subtype of the nicotinic acetylcholine receptor (nAChR) in a subject comprising administering to the subject a therapeutically effective amount of a composition comprising a peptide of the invention.

The invention also provides for a method for reducing pain in a subject comprising administering to the subject a therapeutically effective amount of a composition comprising a peptide of the invention.

The invention also provides for a method for reducing or alleviating pain associated with diabetic neuropathy pain in a subject, comprising administering to the subject a therapeutically effective amount of a composition comprising a peptide of the invention.

The invention also provides for a method for reducing or alleviating chemotherapy-induced pain in a subject, comprising administering to the subject a therapeutically effective amount of a composition comprising a peptide of the invention.

In one embodiment, the peptide blocks the α9α10 subtype of the nAChR.

The invention also provides for a pharmaceutical composition comprising a peptide of the invention, in combination with a pharmaceutically acceptable carrier.

In one embodiment, the invention also provides a peptide comprising an amino acid sequence selected from the group consisting of SEQ ID NO: 2 through SEQ ID NO: 38 and SEQ ID NO: 41.

Thus, the present invention relates to synthetic analgesic peptides that are analogs of the α-conotoxin peptide RgIA. The synthetic analgesic peptides may be isolated or substantially purified. In certain embodiments, the synthetic analgesic peptide of the present invention has an amino acid sequence selected from the group consisting of SEQ ID NO: 2 through SEQ ID NO: 38 and SEQ ID NO: 41.

BRIEF DESCRIPTION OF THE DRAWINGS

The foregoing features of embodiments will be more readily understood by reference to the following detailed description, taken with reference to the accompanying drawings, in which.

DETAILED DESCRIPTION

Definitions

Figure 1:
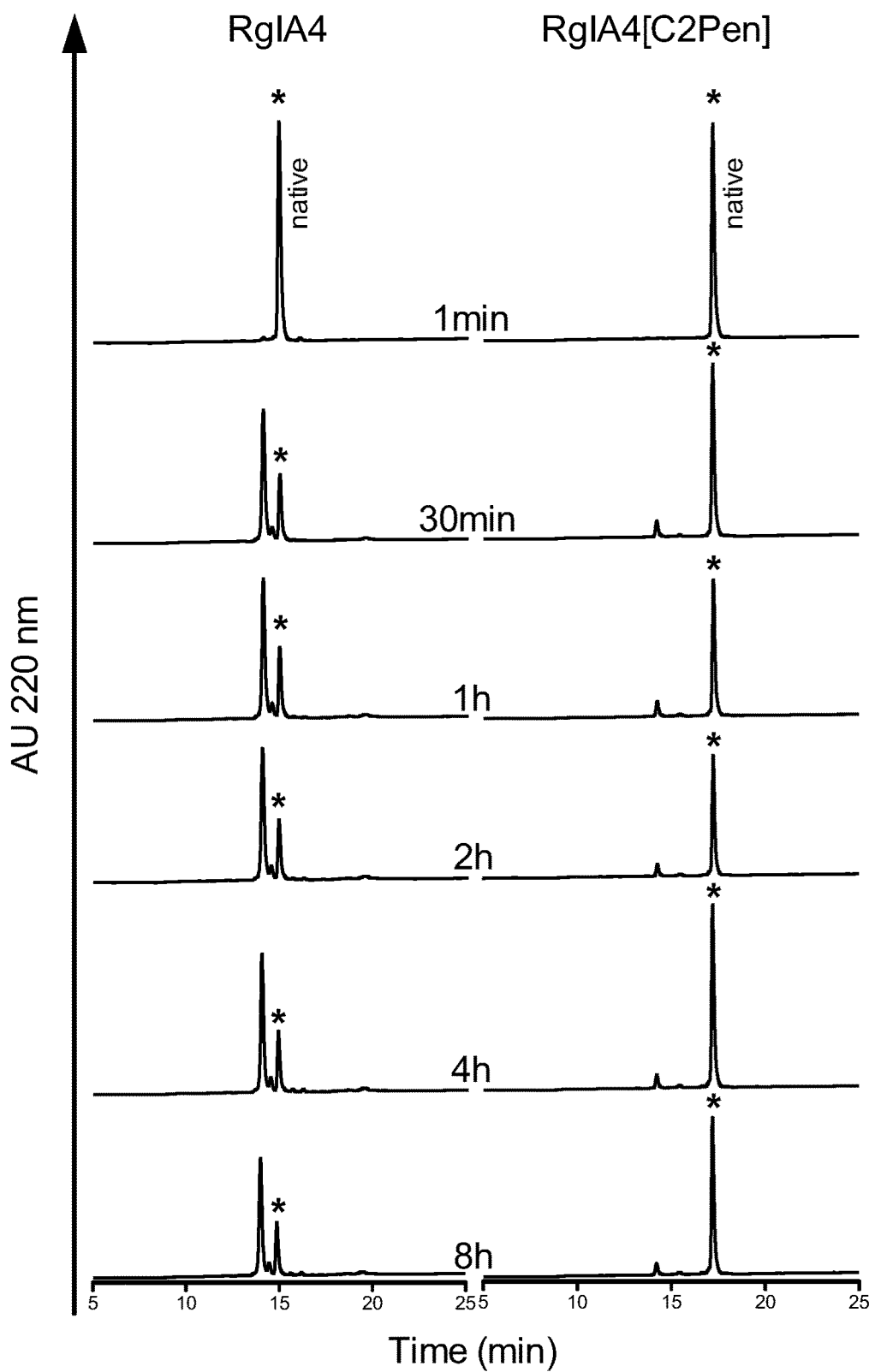
FIG. 1 presents the results of a reverse phase high performance liquid chromatography (HPLC) analysis demonstrating the stability of synthetic analgesic peptides of the invention.

As used in this description and the accompanying claims, the following terms shall have the meanings indicated, unless the context otherwise requires:

A "set" includes at least one member.

"D-substituted analogs" include RgIA analogs disclosed herein having one or more L-amino acids substituted with D-amino acids. The D-amino acid can be the same amino acid type as that found in the analog sequence or can be a different amino acid. Accordingly, D-analogs are also variants.

As used herein, the prefix "des-" means "lacks." For example, "des-X0" means, "lacks residue X0." Thus, for the hypothetical sequence of X0-X1-X2, if X0 is selected from the group consisting of pyroglutamate (pGlu) and des-X0, then the hypothetical sequence encompasses the peptides pGlu-X1-X2 and X1-X2. "A Short Guide to Abbreviations And Their Use In Peptide Science," *Amino Acids, Peptides and Proteins*: Volume 39, 2014, 39, pp. P009-P016

"Modifications" include RgIA analogs disclosed herein wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid (covalent and non-covalent attachment or amalgamation of polyethylene glycol (PEG) polymers), a farnesylated amino acid, an acetylated amino acid, an acylated amino acid, a biotinylated amino acid, a phosphorylated amino acid, an amino acid conjugated to a lipid moiety such as a fatty acid, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, (d) increasing peptide solubility, (e) prolonging circulating time, and/or (f) increasing bioavailability, e.g. increasing the area under the curve (AUCsc). Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications can include derivatives as described elsewhere herein.

"Pharmaceutical compositions" mean physically discrete coherent units suitable for medical administration. "Pharmaceutical composition in dosage unit form" means physically discrete coherent units suitable for medical administration, each containing a therapeutically effective amount, or a multiple (up to four times) or sub-multiple (down to a fortieth) of a therapeutically effective amount of a synthetic analgesic peptide with a pharmaceutically acceptable carrier. Whether the pharmaceutical composition contains a daily dose, or for example, a half, a third or a quarter of a daily dose, will depend on whether the pharmaceutical composition is to be administered once or, for example, twice, three times, or four times a day, respectively.

A "therapeutically effective amount" of a synthetic analgesic peptide is the amount of the synthetic analgesic peptide necessary to achieve a desired physiological response in the subject.

A "prophylactic treatment" includes a treatment administered to a subject who does not display signs or symptoms of pain, an inflammatory condition, inflammation, and/or cancer or a subject who displays only early signs or symptoms of pain, an inflammatory condition, inflammation, and/or cancer such that treatment is administered for the purpose of diminishing, preventing, or decreasing the risk of developing the pain, inflammatory condition, inflammation, and/or cancer further. Thus, a prophylactic treatment functions as a preventative treatment against pain, an inflammatory condition, inflammation, and/or cancer.

A "therapeutic treatment" includes a treatment administered to a subject who displays symptoms or signs of pain, an inflammatory condition, inflammation, and/or cancer and is administered to the subject for the purpose of diminishing or eliminating those signs or symptoms of the pain, inflammatory condition, inflammation, and/or cancer. The therapeutic treatment can reduce, control, or eliminate the presence or activity of pain, an inflammatory condition, inflammation, and/or cancer and/or reduce control or eliminate side effects of pain, an inflammatory condition, inflammation, and/or cancer.

Briefly, the term "gene" refers to a nucleic acid sequence that encodes a peptide. This definition includes various sequence polymorphisms, mutations, and/or sequence variants wherein such alterations do not affect the function of the encoded peptide. The term "gene" may include not only coding sequences but also regulatory regions such as promoters, enhancers, and termination regions. "Gene" further can include all introns and other DNA sequences spliced from the mRNA transcript, along with variants resulting from alternative splice sites. Nucleic acid sequences encoding the peptide can be DNA or RNA that directs the expression of the peptide. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Gene sequences to encode peptides disclosed herein are available in publicly available databases and publications.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

A statement herein that an amino acid is a constituent of a given peptide means that the constituent is an amino acid residue of the peptide.

A candidate for a given occurrence of a variable in a given sequence of amino acids is "independently" selected when the selection of the candidate does not depend on what candidate, if any, has been selected for the variable in any other occurrence of the variable in the given sequence.

A "selection condition" for a given sequence is a specification of rules by which a candidate is chosen for a given occurrence of a variable in the given sequence. When a candidate, for a given occurrence of a variable in a given sequence of amino acids, is "independently" selected as defined above, then the "selection condition" for the given sequence is independently applied for each occurrence of the variable in the given sequence.

A selection condition, by which a given occurrence of a variable in a given sequence of amino acids in a set of amino acid sequences is applied "independently" across the set of sequences, when the selection of the candidate does not depend on what candidate, if any, has been selected for the variable in any other occurrence of the variable in the given sequence or in any other sequence of the set of sequences.

I-3-Y means 3-iodo-tyrosine.

3-R-tyrosine and R-3-Y means a peptide residue selected from the group consisting of 3-chloro-tyrosine, 3-fluoro-tyrosine, 3-iodo-tyrosine, and tyrosine.

The "First Group of Peptide Residues" means the group consisting of L- and D-forms of beta homo-tyrosine, beta homo phenylalanine, beta homo-tryptophan, (3-benzothienyl)-beta-homoalanine, 4,4-diphenyl-beta-homoalanine, (1-naphthyl)-beta-homoalanine, (2-naphthyl)-beta-homoalanine, 4-Styryl-beta-homoalanine, 5-Phenyl-beta-norvaline, 2-Bromo-beta-homophenylalanine, 4-Bromo-beta-homophenylalanine, 2-Chloro-beta-homophenylalanine, 3-Chloro-beta-homophenylalanine, 4-Chloro-beta-homophenylalanine, 2,4-Dichloro-beta-homophenylalanine, 3,4-Dichloro-beta-homophenylalanine, 2-Cyano-beta-homophenylalanine, 3-Cyano-beta-homophenylalanine, 4-Cyano-beta-homophenylalanine, 2-Fluoro-beta-homophenylalanine, 3-Fluoro-beta-homophenylalanine, 4-Fluoro-beta-homophenylalanine, 3,4-Difluoro-beta-homophenylalanine, 4-Iodo-beta-homophenylalanine, 2-Methyl-beta-homophenylalanine, 3-Methyl-beta-homophenylalanine, 4-Methyl-beta-homophenylalanine, 4-Nitro-beta-homophenylalanine, 2-(Trifluoromethyl)-beta-homophenylalanine, 3-(Trifluormethyl)-beta-homophenylalanine, 4-(Trifluoromethyl)-beta-homophenylalanine, 2-Tetrahydroisoquinoline acetic, Tyrosine, Phenylalanine, Tryptophan, Tyrosine, ortho-Tyrosine, 3-nitro-Tyrosine, 3-iodo-Tyrosine, 3-chloro-Tyrosine, 3-fluoro-Tyrosine, 3-amino-Tyrosine, O-methyl-Tyrosine, 2,6-dimethyl-Tyrosine, homomethyl-Phenylalanine, 2-cyano-Phenylalanine, 4-amino-Phenylalanine, 4-acetyl-Phenylalanine, 4-aminomethyl-Phenylalanine, 4-iodo-Phenylalanine, 4-fluoro-Phenylalanine 4-cyano Phenylalanine, 4-guanidine-Phenylalanine, 3,4-dichloro-Phenylalanine, 3,4-difluoro-Phenylalanine, 3,4-dihydroxy-Phenylalanine, 4-methyl-Tryptophan, 5-bromo-Tryptophan, 5-chloro-Tryptophan, 5-fluoro-Tryptophan, 5-hydroxy-Tryptophan, 5-methoxy-Tryptophan and 6-chloro-Tryptophan, (3-benzothienyl)-alanine, 3,3-Diphenyl-alanine, (1-Naphtyl)-alanine, (2-naphthyl)-alanine, 2-Tetrahydroisoquinoline acetic acid, (3-pyridyl)-alanine, and (4-pyridyl)-alanine).

The "Second Group of Peptide Residues" means the group consisting of L- and D-forms of beta homo-tyrosine, beta homo phenylalanine, beta homo-tryptophan, beta-homoarginine, beta-homolysine, (3-benzothienyl)-beta-homoalanine, 4,4-diphenyl-beta-homoalanine, (1-naphthyl)-beta-homoalanine, (2-naphthyl)-beta-homoalanine, 4-Styryl-beta-homoalanine, 5-Phenyl-beta-norvaline, 2-Bromo-beta-homophenylalanine, 4-Bromo-beta-homophenylalanine, 2-Chloro-beta-homophenylalanine, 3-Chloro-beta-homophenylalanine, 4-Chloro-beta-homophenylalanine, 2,4-Dichloro-beta-homophenylalanine, 3,4-Dichloro-beta-homophenylalanine, 2-Cyano-beta-homophenylalanine, 3-Cyano-beta-homophenylalanine, 4-Cyano-beta-homophenylalanine, 2-Fluoro-beta-homophenylalanine, 3-Fluoro-beta-homophenylalanine, 4-Fluoro-beta-homophenylalanine, 3,4-Difluoro-beta-homophenylalanine, 4-Iodo-beta-homophenylalanine, 2-Methyl-beta-homophenylalanine, 3-Methyl-beta-homophenylalanine, 4-Methyl-beta-homophenylalanine, 4-Nitro-beta-homophenylalanine, 2-(Trifluoromethyl)-beta-homophenylalanine, 3-(Trifluormethyl)-beta-homophenylalanine, 4-(Trifluoromethyl)-beta-homophenylalanine, 2-Tetrahydroisoquinoline acetic acid, ortho-Tyrosine, 3-nitro-Tyrosine, 3-iodo-Tyrosine, 3-chloro-Tyrosine, 3-fluoro-Tyrosine, 3-amino-Tyrosine, O-methyl-Tyrosine, tyrosine, 2,6-dimethyl-Tyrosine, homomethyl-Phenylalanine, 2-cyano-Phenylalanine, 4-amino-Phenylalanine, 4-acetyl-Phenylalanine, 4-aminomethyl-Phenylalanine, 4-iodo-Phenylalanine, 4-fluoro-Phenylalanine 4-cyano Phenylalanine, 4-guanidine-Phenylalanine, 3,4-dichloro-Phenylalanine, 3,4-difluoro-Phenylalanine, 3,4-dihydroxy-Phenylalanine, 4-methyl-Tryptophan, 5-bromo-Tryptophan, 5-chloro-Tryptophan, 5-fluoro-Tryptophan, 5-hydroxy-Tryptophan, 5-methoxy-Tryptophan and 6-chloro-Tryptophan, (3-benzothienyl)-alanine, 3,3-Diphenyl-alanine, (1-Naphtyl)-alanine, (2-naphthyl)-alanine, 2-Tetrahydroisoquinoline acetic acid, (3-pyridyl)-alanine, (4-pyridyl)-alanine), ornithine, arginine, norarginine, 2-amino-3-guanidino propionic acid, homoarginine, lysine, ornithine, 2,3-diaminopropanoic acid, diaminobutanoic acid, homolysine, and histidine.

The "Third Group of Peptide Residues" means the group consisting of L- and D-forms of beta-homoarginine, beta-homolysine, arginine, nor-arginine, 2-amino-3-guanidino-propionic acid, homoarginine, lysine, ornithine, 2,3-diaminopropanoic acid, diaminobutanoic acid, homolysine, histidine, (3-pyridyl)-alanine, and (4-pyridyl)-alanine.

Opioids are first-line drugs for moderate to severe acute pain and cancer pain. However, these medications are associated with severe side effects, and whether they are efficacious in treatment of chronic nonmalignant pain remains controversial. The addictive nature of opioids has contributed to the opioid overdose epidemic.

Medications that act through alternative molecular mechanisms are needed. Antagonists of α9α10 nAChRs have been proposed as an important non-opioid mechanism based on studies demonstrating prevention of neuropathology after trauma-induced nerve injury. The inventive peptides are α9α10 nAChR antagonists that offer the following advantages over opioids. The inventive peptides do not have the addictive properties of opioids. Unlike opioids, a subject receiving the inventive peptides will not develop tolerance, and will not experience, or will have reduced, respiratory depression, nausea and other side effects typically associated with opioids. Further, the peptides of the invention can prevent the transition of pain from acute to chronic pain, suggesting a restorative rather than simply a symptomatic management of nerve injury.

The present invention relates to synthetic analgesic peptides that are analogs of the α-conotoxin peptide RgIA. These synthetic analgesic peptides block the α9α10 nAChRs and can be used for treating pain, such as neuropathic pain, for example, diabetic peripheral neuropathic pain, and chemotherapy-induced peripheral neuropathy, inflammatory pain, inflammatory disorders, such as rheumatic diseases, post-surgical pain, migraines, and the treatment of breast cancer. Additional pain conditions include musculoskeletal pain, inflammatory pain, cancer pain, neuropathic pain syndromes including postherpetic neuralgia, idiopathic neuropathic peripheral pain, phantom limb pain, orthopedic pain including osteoarthritis, and autoimmune/inflammatory-induced pain including rheumatoid arthritis pain.

The invention is based on the unexpected finding that the most potent synthetic analgesic peptide analogs have a penicillamine substitution for cysteine at residue position 3 (Cys3).

The synthetic analgesic peptide analogs offer numerous advantages over conotoxin peptide analogs known in the art, for example, analogs having dicarba bridges in place of a cysteine bond. RgIA analogs having non-reducible dicarba bridges in place of native disulfide bonds have been synthesized and analyzed. Disulfide bonds may break and reform with incorrect pairings. This is known as disulfide scrambling and can lead to alterations in the three-dimensional structure, aggregation and function of a peptide. RgIA analogs having dicarba bridges are therefore not subject to this phenomenon (See Chhabra et al. 2014, J. Med. Chem. 57(23): 9933-9944. However, the potency of these dicarba analogs was shown to be significantly lower than that of the natural peptide RgIA. In contrast, the analogs of the invention having a substitution of penicillamine for Cys3 of RgIA4, retain extremely high potency and are significantly more potent than the dicarba analogs.

The synthetic analgesic peptides of the invention offer numerous advantages over conotoxin peptides wherein one or more cysteine reside has been substituted with selenocysteine. Penicillamine use avoids potential selenium toxicity associated with selenocysteine. Although selenium is an essential trace element, exceeding the recommended intake can cause selenosis, with signs that include hair loss, fatigue, irritability and nervous system abnormalities. In addition, it is significantly less costly to prepare penicillamine-substituted peptides, as compared to selenocysteine substituted peptides.

The synthetic analgesic peptides therefore offer the advantages of being more potent, less toxic and/or less expensive to synthesize as compared to known α-conotoxin peptide analogs.

In some embodiments, the invention provides a synthetic analgesic peptide comprising the amino acid sequence G X1 X1 T D P R X1 (Cit)/R (R-3-Y) Q X1 X2 X3 (SEQ ID NO: 2), wherein, with respect to each of the sequences in the set of sequences having SEQ ID NO: 2 through SEQ ID NO: 4, the following selection conditions are applied independently across the set of sequences:

X1 is selected from the group consisting of L-Penicillamine (Pen), D-Penicillamine (D-Pen) and L-Cysteine;
X2 is selected from the group consisting of L-Tyrosine and D-Tyrosine;
X3 is any amino acid,
Cit is citrulline,
R-3-Y is 3-R-tyrosine.

In one embodiment, X3 is selected from the group consisting of L-Arginine and D-Arginine.

In another embodiment, the synthetic analgesic peptide comprises the amino acid sequence G X1 L-Pen T D P R X1 (Cit)/R (R-3-Y) Q X1 X2 X3 (SEQ ID NO: 3).

In another embodiment, the synthetic analgesic peptide comprises the amino acid sequence G X1 D-Pen T D P R X1 (Cit)/R (R-3-Y) Q X1 X2 X3 (SEQ ID NO: 4).

In another embodiment, the C terminal amino acid of the synthetic analgesic peptide is not amidated.

Embodiments of the invention also include a synthetic analgesic peptide comprising an amino acid sequence selected from the group consisting of:

a. G X1 C T D P R C (Cit) (R-3-Y) Q C Y (SEQ ID NO: 5);
b. G C X1 T D P R C (Cit) (R-3-Y) Q C Y (SEQ ID NO: 6);
c. G C C T D P R X1 (Cit) (R-3-Y) Q C Y (SEQ ID NO: 7);
d. G C C T D P R C (Cit) (R-3-Y) Q X1 Y (SEQ ID NO: 8);
e. G X1 C T D P R X1 (Cit) (R-3-Y) Q C Y (SEQ ID NO: 9);
f. G C X1 T D P R C (Cit) (R-3-Y) Q X1 Y (SEQ ID NO: 10);
g. G C X1 T D P R C (Cit) (R-3-Y) Q C X2 X3 (SEQ ID NO: 11);
h. G X1 C T D P R C R (R-3-Y) Q C Y (SEQ ID NO: 12);
i. G C X1 T D P R C R (R-3-Y) Q C Y (SEQ ID NO: 13);
j. G C C T D P R X1 R (R-3-Y) Q C Y (SEQ ID NO: 14);
k. G C C T D P R C R (R-3-Y) Q X1 Y (SEQ ID NO: 15);
l. G X1 C T D P R X1 R (R-3-Y) Q C Y (SEQ ID NO: 16);
m. G C X1 T D P R C R (R-3-Y) Q X1 Y (SEQ ID NO:17); and
n. G C X1 T D P R C R (R-3-Y) Q C X2 X3 (SEQ ID NO: 18);

wherein, with respect to each of the foregoing sequences in the set of sequences having SEQ ID NO: 5 through SEQ ID NO: 18, the following selection conditions are applied independently across the set of sequences:

X1 in at least one occurrence thereof in such sequence, and up to and including all occurrences thereof in such sequence, is in each position independently selected from the group consisting of L-Penicillamine (L-Pen) and D-Penicillamine (D-Pen), and in all other occurrences thereof, if any, is L-Cysteine;
X2 in such sequence is selected from the group consisting of L-Tyrosine and D-Tyrosine;
X3 in such sequence is any amino acid,
Cit is citrulline,
R-3-Y is 3-R-tyrosine.

In one embodiment, X3 is selected from the group consisting of L-Arginine and D-Arginine.

In another embodiment, the C terminal amino acid of the synthetic analgesic peptide is amidated.

In another embodiment, the invention provides for a synthetic analgesic peptide comprising an amino acid sequence selected from the group consisting of:

X0 X1 X2 X3 T D P X4 C (Cit) X5 X6 C X7 (SEQ ID NO: 19);
X0 X1 X2 X3 T D P X4 C X4 X5 X6 C X7 (SEQ ID NO: 20);
X0 X1 X2 X3 T D P X4 C (Cit) X5 X6 C X7 X8 (SEQ ID NO: 21); and
X0 X1 X2 X3 T D P X4 C X4 X5 X6 C X7 X8 (SEQ ID NO: 22);

wherein, with respect to each of the foregoing sequences in the set of sequences having SEQ ID NO: 19 through SEQ ID NO: 22, the following selection conditions are applied independently across the set of sequences:

X0 in such sequence is pyroglutamate or des-X0;
X1 in such sequence is selected from the group consisting of L-Glycine, des-X1, and pyroglutamate;

X2 in such sequence is selected from the group consisting of L-Cysteine, L-Penicillamine and D-Penicillamine;

X3 in such sequence is selected from the group consisting of L-Penicillamine and D-Penicillamine;

X4 in such sequence is, in each position, independently selected from the group consisting of the Third Group of Peptide Residues;

X5 in such sequence is selected from the group consisting of the First Group of Peptide Residues;

X6 in such sequence is selected from the group consisting of L-Glutamine, D-Glutamine, L-Asparagine, D-Asparagine, and the Third Group of Peptide Residues;

X7 in such sequence is selected from the group consisting of L-Tyrosine, D-Tyrosine, a D-beta homo amino acid, an L-beta homo amino acid, the Second Group of Peptide Residues, and the Third Group of Peptide Residues;

X8 in such sequence is selected from the group consisting of an L-amino acid, a D-amino acid, an L-beta homo amino acid, a D-beta homo amino acid, the Second Group of Peptide Residues, and the Third Group of Peptide Residues;

Cit is citrulline; and in the synthetic analgesic peptide, the C-terminal amino acid is selected from the group consisting of amidated amino acids and non-amidated amino acids.

Embodiments of the invention also provide a method for treating or preventing a condition or disorder associate with α9α10 subtype of the nicotinic acetylcholine receptor (nAChR) in a subject comprising administering to the subject a therapeutically effective amount of a composition comprising a peptide of the invention.

Embodiments of the invention also provide a method for reducing pain in a subject comprising administering to the subject a therapeutically effective amount of a composition comprising a peptide of the invention.

Embodiments of the invention also provide a method for reducing or alleviating pain associated with diabetic neuropathy pain in a subject, comprising administering to the subject a therapeutically effective amount of a composition comprising a peptide of the invention.

Embodiments of the invention also provide a method for reducing or alleviating chemotherapy-induced pain in a subject, comprising administering to the subject a therapeutically effective amount of a composition comprising a peptide of the invention.

In one embodiment, the peptide blocks the α9α10 subtype of the nAChR.

Embodiments of the invention also provide a pharmaceutical composition comprising a peptide of the invention, in combination with a pharmaceutically acceptable carrier.

Thus, the present invention relates to synthetic analgesic peptides that are analogs of the α-conotoxin peptide RgIA. The synthetic analgesic peptides may be isolated or substantially purified. In certain embodiments, the synthetic analgesic peptides of the present invention have an amino acid sequence selected from the group consisting of SEQ ID NO: 2 through SEQ ID NO: 38.

RgIA4 (SEQ ID NO: 39) and RgIA5 (GCCTDPRCR(I-3-Y)QCY) (SEQ ID NO: 40) have been demonstrated to be potent inhibitors of α9α10 nAChRs. The peptides of the invention are penicillamine-containing analogs of RgIA4 and RgIA5. The inventive peptides have improved chemical stability as compared to RgIA4 and RgIA5 and are therefore better suited as candidates for further drug development and mechanism of action studies.

The inventive peptides offer the advantages of exhibiting selectivity among nicotinic acetylcholine receptor subtypes and ion channel pain targets, thereby reducing off-target effects.

Disulfide rich peptides like RgIA are prone to isomerization both during chemical synthesis and when used under physiological or basic conditions. Such isomerization leads to lower efficacy of the peptide and therefore limits its further development. The invention is directed to RgIA analogs where Cys3 of RgIA4 and RgIA5 is replaced with penicillamine ("Pen", 3, 3,-Dimethyl-D-cysteine, 3-Mercapto-D-valine), having the formula:

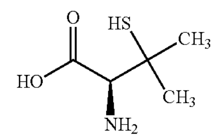

Penicillamine is a sulfur containing amino acid produced during the degradation process of penicillins. The two methyl groups at the β-carbon flanking the thiol group provide conformational constraints to the peptide structure. The resulting penicillamine-substituted peptide analogs exhibit improved stability, and retain activity on α9α10 nAChRs.

Previously described (PCT/US2014/040374) are analogs of RgIA that have desired drug-like characteristics such as increased affinity for the human α9α10 nAChR target compared to the parent RgIA, and increased in vitro and in vivo stability. Previously described RgIA analogs are also disclosed in U.S. Pat. Nos. 6,797,808; 7,279,549; 7,666,840; 7,902,153; 8,110,549; 8,487,075; 8,735,541, 9,717,775 and 9,284,358; and in U.S. patent application Ser. Nos. 12/307,953 and 13/289,494; and WO 2016/073949, each of which is incorporated by reference.

The activity of the α-conotoxins in blocking the α9α10 subtype of the nAChR has been shown in studies using oocytes that express different subtypes of the nAChR. The activity of α-conotoxins in inhibiting migration of immune cells has been shown in studies of chronic constriction injury. α-conotoxins that have been shown to have these activities are α-conotoxin RgIA and α-conotoxin Vc1.1. In addition, α-conotoxin PeIA has been shown to be selective for the α9α10 subtype of the nAChR (McIntosh et al., 2005). Compounds that block the α9α10 nAChR are useful as analgesic agents, as agents for inhibiting the migration of immune cells, as agents for treating inflammatory pain and other inflammatory conditions or disorders and as agents for reducing inflammation associated with disorders such as rheumatic diseases. Inflammatory conditions include, but are not limited to, sepsis, fibromyalgia, inflammatory bowel disease (including; but not limited to ulcerative colitis and Crohn's disease), sarcoidosis, endometriosis, uterine fibroids, inflammatory skin diseases including but not limited to psoriasis, impaired wound healing, inflammatory conditions of the lungs including, but not limited to asthma and chronic obstructive pulmonary disease, diseases associated with inflammation of the nervous system including Parkinson's Disease and Alzheimer's Disease, periodontal disease, and cardiovascular disease. Rheumatic diseases include, but are not limited to, arthritis, lupus, ankylosing spondylitis, fibromyalgia, tendonitis, bursitis, scleroderma, and gout.

Thus, the present invention relates to a method for treating or preventing conditions or disorders associated with the α9α10 subtype of the nicotinic acetylcholine receptor (nAChR) in an individual, which comprises administering to an individual in need thereof a therapeutically effective amount of an active agent or a pharmaceutically acceptable salt thereof, wherein the active agent blocks the α9α10 subtype of the nAChR. In one embodiment, the condition is pain and the administration of the active agent alleviates pain in the individual. In one embodiment, the pain is induced by diabetic peripheral neuropathy. In another embodiment, the pain is induced by chemotherapy induced peripheral neuropathy. In another embodiment, the condition is inflammation mediated by immune cells and the administration of the active agent reduces inflammation. In one embodiment, the inflammation is associated with rheumatic diseases.

Nicotinic Acetylcholine Receptor Subtype α9α10 (nAChR)

The nAChR has been established as a major peripheral pain target (Hone et al. 2017, Br. J. Pharmacol. June 29 doi:10.1111/bph.13931). Preclinical testing has demonstrated the analgesic effects of, and the prevention of pain by antagonists of the nAChR, the pain states being diabetic neuropathy, chemotherapy-induced pain, inflammatory pain, and post-surgical pain. Repeated dosing of peptides leads to cumulative improvement in pain control, unlike opioid tolerance development.

γ-Aminobutyric Acid Type B Receptor (GABA$_B$)

GABA$_B$ receptors (GABA$_B$Rs) are metabotropic G-protein coupled transmembrane receptors that associate with G-proteins that, in turn, regulate specific ion channels. GABA$_B$R mediated inhibition of voltage-gated calcium channels (VGCCs) is an analgesic mechanism of action of conopeptides. The analgesic effects of α-conotoxins and analogs can therefore occur through GABA$_B$R modulation of voltage-gated calcium channels, or through nAChRs (Sadeghi et al. 2017, Neuropharmacol. 127: 116-123).

In certain embodiments, the synthetic analgesic peptides of the invention stimulate GABA$_B$Rs and are used for treating or preventing a condition or disorder associated with GABA$_B$Rs in a subject comprising administering to the subject a therapeutically effective amount of a composition comprising the synthetic analgesic peptide.

Peripheral Pain Indications—Diabetic Neuropathy

Diabetic neuropathy occurs in up to 50% of diabetes patients in the United States (Tesfoye et al. 2012, *Diabetes Metab. Res. Rev.* 28(Suppl 1): 8-14. Damage to peripheral nerves in feet and hands can result from diabetes. The symptoms of diabetic peripheral neuropathy include numbness, sensory loss and shooting or stabbing pain. Complications of diabetic peripheral neuropathy include risk of falls, injury, foot and leg ulcerations, and infection, which can ultimately lead to amputations. Current therapeutic treatments include opioids (43%), anticonvulsants (27%) and antidepressants (18%) (Iyer et al. 2013, *Expert Opin Pharmacother,* 14(13): 1765-75. However, many patients are refractory to these treatments.

Chemotherapy-Induced Pain

Chemotherapy-induced peripheral neuropathy (CIPN) is a frequent, dose-limiting side effect of common cancer chemotherapies including platinum (oxalipatin), vinca alkaloid (vincristine) and taxane (paclitaxel) based compounds. Combinations of two or more of these agents may induce neuropathy in up to 70% of patients (Gupta et al., 2016 BJA Education, Volume 16, Issue 4, pp. 115-119). CIPN causes chronic pain and often sensory, motor and autonomic dysfunction resulting in severe disability. There are currently no known preventatives for CIPN. Anticonvulsants and antidepressants, often used for neuropathic pain, have little or no effect on CIPN. In many patients, opioids are required to control CIPN (Majithia et al. 2016, Oncology Journal Cancer Complications).

Oxaliplatin, a first-line chemotherapy for colorectal cancer and also used to treat ovarian, breast and lung cancers, causes hypersensitivity to cold and often lasts for 3-6 months after cessation of treatment. Vincristine, used primarily for treating solid tumors, lymphomas and leukemias, often causes CIPN.

It has been demonstrated that inhibition of α9α10 nicotinic acid receptor by RgIA4 prevents CIPN and alters disease progression in preclinical animal models (Romero et al. 2017 Proc. Natl. Acad. Sci. USA)

Modifications

In certain embodiments, the peptides of the invention can include one or more modifications, for example, to improve their analgesic and therapeutic activity.

In various embodiments modifications to the RgIA and its analogs are made so as to prevent the isomerization of the conserved aspartate residue to isoaspartate in the conserved tripeptide sequence "Asp-Pro-Arg". This approach prevents this isomerization and results in stable RgIA analogs that maintain their pharmacological properties of high affinity and high selectivity in binding to the intended target, namely α9α10 nAChRs. Therefore, despite the small globular size of RgIA, the peptide bond replacements and the proposed strategies presented hereby result in bioactive, potent, and more stable peptides. Three different chemical approaches are used and evaluated. In the first teaching, the aspartic acid is replaced with amino malonic acid, which is equivalent to an aspartic acid with a shortened side chain. This derivative with the shortened side chain cannot form a 5-membered succinic acid anhydride intermediate that is necessary for production of the isomer. Synthesis can be accomplished via standard peptide chemistry using a suitably protected amino malonic acid.

In the next two approaches, a non-peptide bond is engineered to join the aspartic acid replacement and the proline via N-alkylation of the proline; both examples are non-hydrolysable and therefore not susceptible to isomerization.

The second approach replaces the peptide-chain carbonyl group of aspartic acid with a methylene group to afford a 'reduced peptide bond'. This can be prepared by alkylating the proline with an appropriately protected Asp replacement such as (3S)-4-bromo-3-[[(1, 1-dimethylethoxy)carbonyl]amino]-butanoic acid which itself is incorporated into the peptide chain via standard peptide chemistry.

The third approach replaces the peptide chain carbonyl group of aspartic acid with a ketomethyl group which is the equivalent of inserting a methylene group in the peptide chain between Asp and Pro. This can be done by alkylating the proline with an appropriately protected Asp replacement such as 1, 1-dimethylethyl-(3S)-5-chloro-4-oxo-3-[[(phenylmethoxy)carbonyl]amino]-pentanoate, which itself is incorporated into the peptide chain via standard peptide chemistry.

In various embodiments, amino acid modifications can increase peptide stability by replacement of amino acid residues that may be prone to enzymatic cleavage. Such modifications include: replacement of any L-amino acid with the corresponding D-amino acid; replacement of Gly with a neutral amino acid, including Val, Nor-Val, Leu, or Ile; replacement of Arg with His or Lys; replacement of Pro with Gly; replacement of Gly with Pro, and/or replacement of cysteine with selenocysteine.

In various embodiments, linkers are added to RgIA analog peptides using standard peptide chemistry. The addition of one or more linkers around conserved regions that have been shown to be involved in target recognition increases the stability and binding affinity of RgIA analogs.

In various embodiments the RgIA analogs may have a modification to the N-terminus and/or the C-terminus. Such modifications include: acylation of the N-terminal Gly and/or amidation of the C-terminus; acylation of the N-terminal Gly, replacement of the C-terminal amino acid with the corresponding D-isomer (indicated by a lower case letter), and/or amidation of the C-terminus.

In various embodiments RgIA analogs may be modified by addition of bridges such as lactam bridges or triazole bridges.

The RgIA analogs may also have one cysteine disulfide or one triazole bridge. Each of the cysteine residues are replaced with an amino acid that is a bridge precursor component and contains an alkyne group or an azide group in its side chain, wherein the alkyne group and azide group are coupled to form a 1,2,3-triazole via 1,3-dipolar cycloaddition chemistry. The triazole bridge is formed from a 1,3 dipolar cycloaddition reaction, e.g., "click chemistry."

"Variants" of RgIA analogs disclosed herein include peptides having one or more amino acid additions, deletions, or substitutions, as compared to an RgIA peptide disclosed herein.

An amino acid substitution can be a conservative or a non-conservative substitution. Variants of RgIA analogs disclosed herein can include those having one or more conservative amino acid substitutions. As used herein, a "conservative substitution" involves a substitution found in one of the following conservative substitutions groups: Group 1: alanine (Ala or A), glycine (Gly or G), serine (Ser or S), threonine (Thr or T); Group 2: aspartic acid (Asp or D), glutamic acid (Glu or E); Group 3: asparagine (Asn or N), glutamine (Gln or Q); Group 4: arginine (Arg or R), lysine (Lys or K), histidine (His or H); Group 5: isoleucine (Ile or I), leucine (Leu or L), methionine (Met or M), valine (Val or V); and Group 6: phenylalanine (Phe or F), tyrosine (Tyr or Y), tryptophan (Trp or W).

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) *Proteins*, W.H. Freeman and Company.

Variants of analog conotoxin peptide sequences disclosed or referenced herein also include sequences with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a peptide sequence disclosed or referenced herein. More particularly, variants of the RgIA analogs disclosed herein include peptides that share: 70% sequence identity with any of SEQ ID NOs:1-38; 80% sequence identity with any of SEQ ID NOS:1-38; 81% sequence identity with any of SEQ ID NOs: 1-38; 82% sequence identity with any of SEQ ID NO: 1-38; 83% sequence identity with any of SEQ ID NOs: 1-38; 84% sequence identity with any of SEQ ID NO: 1-38; 85% sequence identity with any of SEQ ID NO: 1-38; 86% sequence identity with any of SEQ ID NO: 1-38; 87% sequence identity with any of SEQ ID NO: 1-38; 88% sequence identity with any of SEQ ID NO: 1-38; 89% sequence identity with any of SEQ ID NO: 1-38; 90% sequence identity with any of SEQ ID NO: 1-38; 91% sequence identity with any of SEQ ID NO: 1-38; 92% sequence identity with any of SEQ ID NO: 1-38; 93% sequence identity with any of SEQ ID NO: 1-38; 94% sequence identity with any of SEQ ID NO:1-38; 95% sequence identity with any of SEQ ID NO: 1-38; 96% sequence identity with any of SEQ ID NO: 1-38; 97% sequence identity with any of SEQ ID NO: 1-38; 98% sequence identity with any of SEQ ID NO: 1-38; or 99% sequence identity with any of SEQ ID NO: 1-38.

Peptides are cleared by the kidneys or phagocytes readily and shortly after administration. Moreover, peptides are susceptible to degradation by proteolytic enzymes.

Linking of peptides to fatty acyl chains (lipidation) of different lengths and structures can increase the half-life of peptides in circulation by promoting interaction with proteins in the blood such as albumin, which act as carriers (See Zorzi et al. 2017, Nat Commun., July 17; 8:16092. doi: 10.1038/ncomms16092). Suitable lipidated moieties include fully saturated lipids as well as unsaturated lipids such as mono-, bis-, tris-, and poly-unsaturated lipids. In some embodiments a core lipid moiety may be conjugated with more than one synthetic analgesic peptide. For example, two of the same synthetic analgesic peptides may be conjugated to a single lipid moiety.

An activated ester of a fatty acid, such as a N-Hydroxysuccinimidyl ester or other activated ester derived from a fatty acid with a free carboxylic acid and a commercially available peptide coupling reagent, is mixed with the synthetic analgesic peptide of interest that contains a free amine such as N-terminal glycine in a solvent such as dimethylformamide and a base like diisopropylethylamine. The mixture is stirred in the dark for 12-16 hours and the lipidated synthetic analgesic peptide product is isolated by semi-preparative reversed phase chromatography.

Modifications of RgIA analogs described herein also include fusion of the peptide to the Fc domain of IgG, thus combining the biological activity of the RgIA peptides with the stability of monoclonal antibodies. As described herein, these RgIA peptibodies would be generated by recombinant technology by fusing an RgIA analog in-frame with the Fc portion of human IgG. These peptide-Fc fusion proteins generally have a molecular weight of less than 60-70 kDa, or approximately half the weight of monoclonal antibodies. Incorporation of the Fc portion of IgG in peptibodies can prolong the half-life through FcRn protection. Dimerization of two Fc regions increases the number of active peptides interacting with the target up to two-fold (Wu et al., 2014).

In certain embodiments, the peptide is fused to other domains of IgG or to albumin.

The presence of modified amino acids may be advantageous in, for example, (a) increasing peptide serum half-life and/or functional in vivo half-life, (b) reducing peptide immunogenicity, (c) increasing peptide storage stability, (d) increasing peptide solubility, (e) prolonging circulating time, (f) increasing bioavailability, e.g. increasing the area under the curve (AUCsc), and/or (g) increased buccal or oral bioavailability by increasing mucosal absorption. Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications can include derivatives as described elsewhere herein.

The C-terminus of a synthetic analgesic peptide may be a carboxylic acid or an amide group. The present disclosure also relates to RgIA analogs further modified by (i) additions made to the C-terminus, such as tyrosine, 3-iodo-tyrosine, a fluorescent tag, lipids, carbohydrates, or beta-homo amino acids and/or (ii) additions made to the N-terminus, such as tyrosine, 3-iodo-tyrosine, pyroglutamate, a fluorescent tag, lipids, carbohydrates, or beta-homo amino acids.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus.

In certain embodiments, modification of the N-terminus includes acylation including N-formyl, N-acetyl, N-propyl, and long chain fatty acid groups. In certain embodiments modification of the N-terminus includes addition of a pyroglutamate group. In certain embodiments, modification of the C-terminus and/or N-terminus includes lipidation by the addition of fatty acids 4 to 24, 10 to 18, or 12 to 16 carbon atoms in length.

In certain embodiments, modification of the peptide includes linkage of the peptide to fluorescent labels, including fluorescent dyes.

In certain embodiments, modification of the peptide includes replacement of one or more of the disulfide bonds with one or more of the following: dicarba bridges as alkane (via hydrogenation of alkene), Z-alkene, E-alkene, thioether, selenoether, trisulfide, tetrasulfide, polyethoxy ether, aliphatic linkers, and/or a combination of aliphatic linker with one or more alkene moieties (Z- or E-isomers) that are synthesized via ring-closing metathesis reactions.

In certain embodiments, modification of the peptide includes PEGylation. PEGylation consists of the addition of one or more poly-(ethylene glycol) (PEG) molecules to a peptide or protein, and often enhances protein and peptide delivery (Davies et al., 1977).

Peptides are cleared by the kidneys phagocytes readily and shortly after administration. Moreover, peptides are susceptible to degradation by proteolytic enzymes in the blood. Linking of peptides to polyethylene glycol of different lengths and structures can increase the half-life of peptides in circulation. PEGylation increases the molecular weight of the peptide and thus reduces the rate with which it is filtrated in the kidneys; PEGylation can also shield the peptide from proteases and macrophages and other cells of the reticuloendothelial system (RES) that can remove it. In addition, PEGylation may reduce any immunogenicity associated with a foreign peptide.

An example of how synthetic analgesic peptides can be conjugated to PEG is conjugation of a methoxy poly(ethylene glycol)-succinimidyl valerate to synthetic analgesic peptide. 5-10 mg of synthetic analgesic peptide and mPEG-butyraldehyde are reacted at a 1.5:1 molar ratio by stirring in 0.25 ml of anhydrous dimethyl formamide in the presence of 0.0026 ml N,N-diisopropylethylamine at room temperature for 16 hours in the dark. Reaction completeness and the concentration of PEGylated synthetic analgesic peptide is measured by reverse phase chromatography using a Poroshell C18 column. In another type of PEG conjugation reaction, a methoxy poly(ethylene glycol) (i.e., PEG)-butyraldehyde is joined to a synthetic analgesic peptide. 5-10 mg of a synthetic analgesic peptide and mPEG-butyraldehyde are reacted at a 1.5:1 molar ratio by stirring in 0.2 ml of 100% methanol at room temperature for 15 minutes. An aqueous solution of sodium cyanoborohydride is added to a final concentration of 1 mg/ml, followed by mixing 16 hours at room temperature in the dark. Reaction completeness and the concentration of PEGylated-synthetic analgesic peptide is measured by reverse phase chromatography using a Poroshell C18 column. mPEG-conjugated synthetic analgesic peptides are purified by removal of excess synthetic analgesic peptide by centrifugation in a desalting column. Samples are centrifuged at 1000×g for 2 minutes in a methanol-equilibrated Zeba Spin desalting column, (2 ml volume, 7,000 molecular weight cut-off, ThermoScientific). Reaction completeness and the concentration of PEGylated synthetic analgesic peptide in spun-through material is measured by reverse phase chromatography using a Poroshell C18 column.

Various other strategies may be employed to extend the half-life of peptides by fusing them to conjugates that extend half-life. These half-life extending conjugates include fusion of the peptide to the C-terminus or N-terminus of human IgG Fc, fusion of the peptide to the C-terminus or N-terminus of HSA, fusion of the peptide to the C-terminus or N-terminus of human transferrin, fusion of the peptide to a non-exact repeat peptide sequence (XTENylation), fusion of the peptide to a polypeptide sequences composed of PAS (XL-Protein GmbH) (PASylation), fusion to an ELP repeat sequence (PhaseBio) (ELPylation), fusion of the peptide to HAP (e.g., homopolymer of glycine residues) (HAPylation), fusion of the peptide with GLK, and fusion with the CTP peptide from human CG β-subunit. See Strohl *BioDrugs* (2015) 29:215-239.

In some embodiments, conjugates that extend the half-life of the peptides of the invention, including but not limited to the aforementioned half-life extending conjugates, fatty acyl chains, albumin, and polyethylene glycol, may be conjugated to the peptide at the N-terminus, the C-terminus, or both the N- and C-termini. In addition, half-life extending conjugates may be conjugated to internal residues of the peptides, either alone, or in conjunction with N- and/or C-terminal fusions.

In an exemplary embodiment, half-life extending conjugates may be conjugated to Thr4 of SEQ ID NO: 37, Gln11 of SEQ ID NO: 37, or both Thr4 and Gln11 of SEQ ID NO: 37. Homologous threonine and glycine residues of SEQ ID NO: 2-36, SEQ ID NO: 38, and SEQ ID NO: 41 may also be conjugated to half-life extending conjugates in similar fashion. Such homologous residues will be readily apparent to one of skill in the art.

The present disclosure is further directed to derivatives of the disclosed RgIA analogs. Derivatives include RgIA analogs having cyclic permutations in which the cyclic permutants retain the native bridging pattern of native conotoxin peptide (Craik, et al. (2001)), e.g., a cyclized synthetic analgesic peptide having an amide cyclized backbone such that the synthetic analgesic peptide has no free N- or C-terminus, in which the synthetic analgesic peptide includes the native disulfide bonds (U.S. Pat. No. 7,312,195, incorporated by reference herein). In one embodiment, the cyclized synthetic analgesic peptide includes a linear synthetic analgesic peptide and a peptide linker, wherein the N- and C-termini of the linear synthetic analgesic peptide are linked via the peptide linker to form the amide cyclized peptide backbone.

In some embodiments, the peptide linker includes amino acids selected from glycine, alanine and combinations thereof.

Various cyclization methods can be applied to the RgIA analogs described herein. The RgIA analogs described herein can be readily cyclized using alanine bridges as described in, for example, Clark, et al., 2013, and Clark, et al., 2012. Cyclizing RgIA analogs can improve their oral bioavailability and reduce the susceptibility to proteolysis, without affecting the affinity of the RgIA analogs for their specific targets. In some embodiments, cyclization occurs between the N- and C-termini via an amino acid linker that joins the N- and C-termini, where the cyclization linker can be of any length between 1 and 8 amino acids and can be composed of any amino acid sequence. In certain embodiments, cyclization is done using alternative linkers such as non-peptide linkers including polyethoxy ethers, aliphatic linkers, and/or any combination of aliphatic linker with one or more alkene moieties (Z- or E-isomers) in the hydrocarbon chain that can be synthesized via ring-closing metathesis reactions.

Embodiments disclosed herein include the RgIA analogs described herein as well as variants, D-substituted analogs, modifications, and derivatives of the RgIA analogs described herein. In some embodiments, variants, D-substituted analogs, modifications, and derivatives have 1, 2, 3, 4, 5, 6, 7, 8, 9, 10, 11, 12, 13, 14, 15, 16, 17, or 18 sequence additions, deletions, substitutions, replacements, conjugations, associations, or permutations. Each synthetic analgesic peptide disclosed herein may also include additions, deletions, substitutions, replacements, conjugations, associations, or permutations at any position including positions 1, 2, 3, 4, 5, 6, 7, 8, 9, 10, 11, 12, 13, 14, 15, 16, 17, or 18 of an analog synthetic analgesic peptide sequence disclosed herein.

In some embodiments an Xaa position can be included in any position of an synthetic analgesic peptide, wherein Xaa represents an addition, deletion, substitution, replacement, conjugation, association or permutation. In particular embodiments, each analog synthetic analgesic peptide has 1, 2, 3, 4, 5, 6, 7, 8, 9, 10, 11, 12, 13, 14, 15, 16, 17, or 18 Xaa positions at one or more of positions 1, 2, 3, 4, 5, 6, 7, 8, 9, 10, 11, 12, 13, 14, 15, 16, 17, or 18.

An analog can have more than one change (addition, deletion, substitution, replacement, conjugation, association, or permutation) and qualify as one or more of a variant, D-substituted analog, modification, and/or derivative. That is, inclusion of one classification of analog, variant, D-substituted analog, modification and/or derivative is not exclusive to inclusion in other classifications and all are collectively referred to as “synthetic analgesic peptides” herein.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus.

The present invention is further directed to derivatives of the above peptides which are acylic permutations in which the cyclic permutants retain the native bridging pattern of native conotoxin peptide (Craik et al. (2001), e.g., a cyclized synthetic analgesic peptide having an amide cyclized backbone such that the synthetic analgesic peptide has no free N- or C-terminus in which the synthetic analgesic peptide comprises the native disulfide bonds (U.S. Pat. No. 7,312,195). In one embodiment, the cyclized synthetic analgesic peptide comprises a linear synthetic analgesic peptide and a peptide linker, wherein the N- and C-termini of the linear synthetic analgesic peptide are linked via the peptide linker to form the amide cyclized peptide backbone. In some embodiments, the peptide linker comprises amino acids selected from the group consisting of glycine, alanine and combinations thereof.

The synthetic analgesic peptides can be prepared using recombinant DNA technology. Synthetic analgesic peptides may also be prepared using Merrifield solid-phase synthesis, although other equivalent chemical syntheses known in the art can also be used. Solid-phase synthesis is commenced from the C-terminus of the synthetic analgesic peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al. (1966). Chloromethylated resins are commercially available from Bio Rad Laboratories (Richmond, Calif.). The preparation of such a resin is described by Stewart and Young (1969). BHA and MBHA resin supports are commercially available, and are generally used when the desired synthetic analgesic peptide being synthesized has an unsubstituted amide at the C-terminus. Thus, solid resin supports may be any of those known in the art, such as one having the formulae —OCH2- resin support, —NH BHA resin support, or —NH-MBHA resin support. When the unsubstituted amide is desired, use of a BHA or MBHA resin can be advantageous because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it is possible to synthesize the synthetic analgesic peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in dimethylformamide (DMF) at about 60° C. for 24 hours with stirring, when a synthetic analgesic peptide having free acid at the C-terminus is to be synthesized. Following the coupling of the BOC-protected amino acid to the resin support, the α-amino protecting group can be removed, as by using trifluoroacetic acid (TFA) in methylene chloride or TFA alone. The deprotection can be carried out at a temperature between 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids can be coupled step-wise in the desired order to obtain an intermediate compound or, as an alternative to adding each amino acid separately in the synthesis, some of them may be coupled to one another prior to addition to the solid phase reactor. Selection of an appropriate coupling reagent is within the skill of the art. Illustrative coupling reagents include N,N'-dicyclohexylcarbodiimide (DCC, DIC, HBTU, HATU, TBTU in the presence of HOBt or HOAt).

The activating reagents used in the solid phase synthesis of peptides are well known in the art. Examples of suitable activating reagents include carbodiimides, such as N,N'-diisopropylcarbodiimide and N-ethyl-N'-(3-dimethylaminopropyl) carbodiimide. Other activating reagents and their use in peptide coupling are described by Montalbetti, 2005, Tetrahedron 61: 10827-10852 and El-Faham et al. 2011, Chem. Rev. 111: 6557-602.

Each protected amino acid or amino acid sequence can be introduced into the solid-phase reactor in a twofold or more excess, and the coupling may be carried out in a medium of DMF:$CH_2Cl_2$ (1:1) or in DMF or $CH_2Cl_2$ alone. In cases where intermediate coupling occurs, the coupling procedure can be repeated before removal of the α-amino protecting group prior to the coupling of the next amino acid. The success of the coupling reaction at each stage of the synthesis, if performed manually, can be monitored by the ninhydrin reaction, as described by Kaiser, et al. (1970). Coupling reactions can be performed automatically, as on a Beckman 990 automatic synthesizer, using a program such as that reported in Rivier, et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group can be first removed using TFA/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide can be included in the reaction vessel.

Cyclization of the linear synthetic analgesic peptide can be affected (as opposed to cyclizing the synthetic analgesic peptide while a part of the peptido-resin) to create bonds between Cys residues. To affect such a disulfide cyclizing linkage, a fully protected synthetic analgesic peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the synthetic analgesic peptide from the above resins or a benzhydrylamine (BHA) resin or a methylbenzhydrylamine (MBHA), can take place at 0° C. with hydrofluoric acid (HF) or TFA, followed by oxidation. Chan, P. D. White *Fmoc Solid Phase Peptide Synthesis—A Practical Approach* Oxford University Press, Oxford (2000)

The synthetic analgesic peptides can also be synthesized using an automatic synthesizer. In these embodiments, amino acids can be sequentially coupled to an MBHA Rink resin (typically 100 mg of resin) (or another type of resin, for example Wang resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1, 1,3,3-tetramethyluronium hexafluorophosphate (HBTU) and diethylisopropylethylamine (DIEA). The Fmoc protecting group can be removed by treatment with a 20% solution of piperidine in dimethylformamide (DMF). Resins are subsequently washed with DMF (twice), followed by methanol and NMP.

Pharmaceutical Compositions

Synthetic analgesic peptides can be formulated within pharmaceutical compositions.

The amount and concentration of a synthetic analgesic peptide in a pharmaceutical composition, as well as the quantity of the pharmaceutical composition can be selected based on clinically relevant factors, the solubility of the synthetic analgesic peptide in the pharmaceutical composition, the potency and activity of the synthetic analgesic peptide, and the manner of administration of the pharmaceutical composition. It is only necessary that the synthetic analgesic peptide constitute a therapeutically effective amount, i.e., such that a suitable effective dosage will be consistent with the dosage form employed in single or multiple unit doses.

The pharmaceutical compositions will generally contain from 0.0001 to 99 wt. %, preferably 0.001 to 50 wt. % or from 0.01 to 10 wt. % of the synthetic analgesic peptide by weight of the total composition. In addition to the synthetic analgesic peptide, the pharmaceutical compositions can also contain other drugs or agents. Examples of other drugs or agents include analgesic agents, cytokines, and therapeutic agents in all of the major areas of clinical medicine. When used with other drugs or agents, the synthetic analgesic peptides may be delivered in the form of drug cocktails. A cocktail is a mixture of any one of the synthetic analgesic peptides with another drug or agent. In this embodiment, a common administration vehicle (e.g., pill, tablet, implant, pump, injectable solution, etc.) would contain both the synthetic analgesic peptide in combination with the other drugs or agents. The individual components of the cocktail can each be administered in therapeutically effective amounts or their administration in combination can create a therapeutically effective amount.

Pharmaceutical compositions include pharmaceutically acceptable carriers including those that do not produce significantly adverse, allergic, or other untoward reactions that outweigh the benefit of administration, whether for research, prophylactic, and/or therapeutic treatments. Illustrative pharmaceutically acceptable carriers and formulations are disclosed in Remington, 2005. Moreover, pharmaceutical compositions can be prepared to meet sterility, pyrogenicity, and/or general safety and purity standards as required by U.S. Food and Drug Administration (FDA) Office of Biological Standards, and/or other relevant regulatory agencies.

Typically, a synthetic analgesic peptide will be admixed with one or more pharmaceutically acceptable carriers chosen for the selected mode of administration. For examples of delivery methods see U.S. Pat. No. 5,844,077, which is incorporated by reference.

Illustrative generally used pharmaceutically acceptable carriers include any and all bulking agents, fillers, solvents, co-solvents, dispersion media, coatings, surfactants, antioxidants, preservatives, isotonic agents, releasing agents, absorption delaying agents, salts, stabilizers, buffering agents, chelating agents, gels, binders, disintegration agents, wetting agents, emulsifiers, lubricants, coloring agents, flavoring agents, sweetening agents, and perfuming agents.

Illustrative buffering agents include citrate buffers, succinate buffers, tartrate buffers, fumarate buffers, gluconate buffers, oxalate buffers, lactate buffers, acetate buffers, phosphate buffers, histidine buffers, and trimethylamine salts.

Illustrative preservatives include phenol, benzyl alcohol, meta-cresol, methyl paraben, propyl paraben, octadecyldimethylbenzyl ammonium chloride, benzalkonium halides, hexamethonium chloride, alkyl parabens, methyl paraben, propyl paraben, catechol, resorcinol, cyclohexanol, and 3-pentanol.

Illustrative isotonic agents include polyhydric sugar alcohols, trihydric sugar alcohols, or higher sugar alcohols, such as glycerin, erythritol, arabitol, xylitol, sorbitol, and mannitol.

Illustrative stabilizers include organic sugars, polyhydric sugar alcohols, polyethylene glycol, sulfur-containing reducing agents, amino acids, low molecular weight peptides, immunoglobulins, hydrophilic polymers, and polysaccharides.

Illustrative antioxidants include ascorbic acid, methionine, vitamin E, cysteine hydrochloride, sodium bisulfite, sodium metabisulfite, sodium sulfite, oil soluble antioxidants, ascorbyl palmitate, butylated hydroxyanisole (BHA), butylated hydroxytoluene (BHT), lecithin, propyl gallate, alpha-tocopherol, metal chelating agents, citric acid, ethylenediamine tetraacetic acid (EDTA), sorbitol, tartaric acid, and phosphoric acid.

Illustrative lubricants include sodium lauryl sulfate and magnesium stearate.

Illustrative pharmaceutically acceptable salts include acidic and/or basic salts, formed with inorganic or organic acids and/or bases, preferably basic salts. While pharmaceutically acceptable salts are preferred, particularly when employing the synthetic analgesic peptides as medicaments, other salts find utility, for example, in processing these synthetic analgesic peptides, or where non-medicament-type uses are contemplated. Salts of these synthetic analgesic peptides may be prepared by techniques recognized in the art.

Illustrative pharmaceutically acceptable salts include inorganic and organic addition salts, such as hydrochloride, sulphates, nitrates, phosphates, acetates, trifluoroacetates, propionates, succinates, benzoates, citrates, tartrates, fumarates, maleates, methane-sulfonates, isothionates, theophylline acetates, and salicylates. Lower alkyl quaternary ammonium salts can also be used.

For oral administration, the synthetic analgesic peptides can be formulated into solid or liquid preparations such as capsules, pills, tablets, lozenges, melts, powders, suspensions, or emulsions. In preparing the compositions in oral dosage form, any of the usual pharmaceutically acceptable carriers may be employed, such as, for example, carriers such as starches, sugars, diluents, granulating agents, lubricants, binders, disintegrating agents, and the like in the case of oral solid preparations (such as, for example, powders, capsules and tablets); or water, glycols, oils, alcohols, flavoring agents, preservatives, coloring agents, suspending agents, and the like in the case of oral liquid preparations (such as, for example, suspensions, elixirs and solutions). Because of their ease in administration, tablets and capsules can represent an advantageous oral dosage unit form, in which case solid pharmaceutical carriers are obviously employed. If desired, tablets may be sugar-coated or enteric-coated by standard techniques. The synthetic analgesic peptide can be encapsulated to make it stable to passage through the gastrointestinal tract while at the same time, in certain embodiments, allowing for passage across the blood brain barrier. See for example, WO 96/11698.

For parenteral administration, the synthetic analgesic peptides may be dissolved in a pharmaceutically acceptable carrier and administered as either a solution or a suspension. Illustrative pharmaceutically acceptable carriers include water, saline, dextrose solutions, fructose solutions, ethanol, or oils of animal, vegetative, or synthetic origin. The carrier may also contain other ingredients, for example, preservatives, suspending agents, solubilizing agents, buffers, and the like.

The synthetic analgesic peptides can be in powder form for reconstitution in the appropriate pharmaceutically acceptable carrier at the time of delivery. In another embodiment, the unit dosage form of the synthetic analgesic peptide can be a solution of the synthetic analgesic peptide, or a pharmaceutically acceptable salt thereof, in a suitable diluent in sterile, hermetically sealed ampoules or sterile syringes.

Synthetic analgesic peptides can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, synthetic analgesic peptides can be formulated as sustained-release systems utilizing semipermeable matrices of solid polymers containing at least one compound. Various sustained-release materials have been established and are well known by those of ordinary skill in the art. Sustained-release systems may, depending on their chemical nature, release synthetic analgesic peptides following administration for a few weeks up to over 100 days.

Administration of the synthetic analgesic peptide can also be achieved using pumps (see, e.g., Luer et al., (1993), Zimm, et al. (1984) and Ettinger, et al. (1978)); microencapsulation (see, e.g., U.S. Pat. Nos. 4,352,883, 4,353,888, and 5,084,350); continuous release polymer implants (see, e.g., U.S. Pat. No. 4,883,666); and macroencapsulation (see, e.g., U.S. Pat. Nos. 5,284,761, 5,158,881, 4,976,859, and 4,968,733 and published PCT patent applications WO92/19195, WO 95/05452), each of which is incorporated by reference herein.

When the synthetic analgesic peptides are administered intrathecally, they may also be dissolved in cerebrospinal fluid. Naked or unencapsulated cell grafts to the CNS can also be used. See, e.g., U.S. Pat. Nos. 5,082,670 and 5,618,531, each of which is incorporated by reference herein.

The synthetic analgesic peptides of the present disclosure, and pharmaceutical compositions thereof, are useful in methods of treating conditions associated with the α9α10 receptor subtype of the nicotinic acetylcholine receptor (nAChR) in a subject. The activity of RgIA and its analogs in blocking the α9α10 subtype of nAChR has been shown in studies using oocytes that express different subtypes of the nAChR (Ellison et al., 2006; Vincler et al., 2006; WO 2008/011006; US 2009/0203616; US 2012/0220539, each of which is incorporated by reference herein). The activity of α-conotoxins, including RgIA, as an antinociceptive and an analgesic has been shown in studies of chronic constriction injury (Vincler, et al., 2006; WO 2008/011006; US 2009/0203616, each of which is incorporated by reference herein). The activity of α-conotoxins, including RgIA, in inhibiting migration of immune cells has been shown in studies of chronic constriction injury (Vincler, et al., 2006; WO 2008/011006; US 2009/0203616, each of which is incorporated by reference herein).

Methods described herein include administering to a subject in need thereof a therapeutically effective amount of a disclosed synthetic analgesic peptide or a pharmaceutically acceptable salt thereof, wherein the disclosed synthetic analgesic peptide blocks the α9α10 subtype of the nAChR. Synthetic analgesic peptides that block the α9α10 subtype of nAChR are useful for treating pain, for treating inflammation and/or inflammatory conditions and for treating cancers and/or cancer related pain. In certain embodiments, the synthetic analgesic peptides are effective based on their ability to inhibit the migration of immune cells. In other embodiments, the compounds are effective based on their ability to slow demyelination and/or increase the number of intact nerve fibers.

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.)) with synthetic analgesic peptides disclosed herein including pharmaceutically-acceptable salts and prodrugs thereof. Treating subjects includes delivering therapeutically effective amounts of the disclosed synthetic analgesic peptides. Therapeutically effective amounts include those that provide effective amounts, prophylactic treatments, and/or therapeutic treatments.

Illustrative types of pain that can be treated include general pain, chronic pain, neuropathic pain, nociceptive pain, and inflammatory pain. In addition, these types of pain can be associated with and/or induced by causes including: peripheral nerve or nociceptor damage, inflammatory conditions, metabolic disorders, virus infection, cancers, pain induced by chemotherapeutic agents, pain induced after surgical procedure, and pain induced by burn or other physical tissue injury.

Therapeutically effective amounts in the treatment of chemotherapy-induced neuropathic pain (CINP) can include those that decrease mechanical hyperalgesia, mechanical allodynia (pain due to a stimulus that does not normally cause pain), thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of burn-induced neuropathic pain can include those that decrease mechanical hyperalgesia, mechanical allodynia, thermal (heat induced) hyperalgesia, thermal (cold-induced) allodynia, the number of migrating immune cells, levels of inflammatory mediators, and/or subject-reported subjective pain levels.

Therapeutically effective amounts in the treatment of post-operative neuropathic pain can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Illustrative inflammatory conditions that can be treated include inflammation, chronic inflammation, rheumatic diseases (including arthritis, lupus, ankylosing spondylitis, fibromyalgia, tendonitis, bursitis, scleroderma, and gout), sepsis, fibromyalgia, inflammatory bowel disease (including ulcerative colitis and Crohn's disease), sarcoidosis, endometriosis, uterine fibroids, inflammatory skin diseases (including psoriasis and impaired wound healing), inflammatory conditions of the lungs (including asthma and chronic obstructive pulmonary disease), diseases associated with inflammation of the nervous system (including multiple sclerosis, Parkinson's Disease and Alzheimer's Disease), periodontal disease, and cardiovascular disease.

Therapeutically effective amounts in the treatment of inflammatory conditions can include those that decrease levels of inflammatory markers at the gene expression or protein level and/or reduce the number of migrating immune cells. In addition, pain associated with inflammatory conditions can be treated by therapeutically effective amounts that result in the decrease of mechanical hyperalgesia, mechanical allodynia, thermal (heat-induced) hyperalgesia, thermal (cold-induced) allodynia, and/or subject-reported subjective pain levels.

Illustrative cancers that can be treated include breast cancers. α9-nAChR is overexpressed in human breast tumor tissue (Lee et al., 2010a) and receptor inhibition by siRNA or other mechanism reduced in vitro and in vivo carcinogenic properties of breast cancer cells, including inhibition of cancer cell proliferation (Chen et al., 2011). In certain embodiments, RgIA analogs are used in therapeutic amounts in order to inhibit tumor growth by inhibition of α9-nAChR.

Therapeutically effective amounts in the treatment of cancers, such as breast cancers, can include those that decrease a number of tumor cells, decrease the number of metastases, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation, inhibit tumor growth, prevent metastasis, prolong a subject's life, reduce cancer-associated pain, and/or reduce relapse or reoccurrence of the cancer in a subject following treatment.

For administration, therapeutically effective amounts can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine therapeutically effective amounts in subjects of interest.

The actual amount administered to a particular subject as a therapeutically effective amount can be determined by a physician, veterinarian, or researcher taking into account parameters such as physical and physiological factors including target; body weight; severity of condition; type of pain, inflammatory condition, or cancer; previous or concurrent therapeutic interventions; idiopathy of the subject; and route of administration.

Dosage may be adjusted appropriately to achieve desired synthetic analgesic peptide levels, locally or systemically. Typically the synthetic analgesic peptides of the present disclosure exhibit their effect at a dosage range from 0.001 mg/kg to 250 mg/kg, preferably from 0.01 mg/kg to 100 mg/kg of the synthetic analgesic peptide, more preferably from 0.05 mg/kg to 75 mg/kg. A suitable dose can be administered in multiple sub-doses per day. Typically, a dose or sub-dose may contain from 0.1 mg to 500 mg of the synthetic analgesic peptide per unit dosage form. A more preferred dosage will contain from 0.5 mg to 100 mg of synthetic analgesic peptide per unit dosage form.

Additional doses which are therapeutically effective amounts can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

In particular embodiments, dosages can be initiated at lower levels and increased until desired effects are achieved. In the event that the response in a subject is insufficient at such doses, even higher doses (or effective higher doses by a different, more localized delivery route) may be employed to the extent that subject tolerance permits. Continuous dosing over, for example, 24 hours, or multiple doses per day are contemplated to achieve appropriate systemic levels of synthetic analgesic peptide.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

A variety of administration routes are available. The particular mode selected can depend upon the particular synthetic analgesic peptide delivered, the severity of pain, inflammatory condition or cancer being treated, and the dosage required to provide a therapeutically effective amount. Any mode of administration that is medically acceptable, meaning any mode that provides a therapeutically effective amount of the synthetic analgesic peptide without causing clinically unacceptable adverse effects that outweigh the benefits of administration according to sound medical judgment, can be used. Illustrative routes of administration include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

In one embodiment, the synthetic analgesic peptide is delivered directly into the central nervous system (CNS), preferably to the brain ventricles, brain parenchyma, the intrathecal space, or other suitable CNS location.

Alternatively, targeting therapies may be used to deliver the synthetic analgesic peptide more specifically to certain types of cells, by the use of targeting systems such as antibodies or cell specific ligands.

Synthetic analgesic peptides can also be administered in a cell based delivery system in which a nucleic acid sequence encoding the synthetic analgesic peptide is introduced into cells designed for implantation in the body of the subject. In particular embodiments, this delivery method can be used in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959, and WO 97/12635, each of which is incorporated by reference herein.

Suitable nucleic acid sequences can be prepared synthetically for each synthetic analgesic peptide on the basis of the disclosed sequences and the known genetic code. In some embodiments, the polynucleotide includes a plasmid, a cDNA, or an mRNA that can include, e.g., a sequence (e.g., a gene) for expressing a synthetic analgesic peptide. Suitable plasmids include standard plasmid vectors and minicircle plasmids that can be used to transfer a gene to a cell. The polynucleotides (e.g., minicircle plasmids) can further include any additional sequence information to facilitate transfer of the genetic material (e.g., a sequence encoding a synthetic analgesic peptide) to a cell. For example, the polynucleotides can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques. As described further herein, the polynucleotides can be used to transfect cells. Unless otherwise specified, the terms transfect, transfected, or transfecting can be used to indicate the presence of exogenous polynucleotides or the expressed polypeptide therefrom in a cell. A number of vectors are known to be capable of mediating transfer of genes to cells, as is known in the art.

As stated, synthetic analgesic peptides disclosed herein block the $\alpha 9\alpha 10$ subtype of the nAChR. Blocking can be measured by any effective means. In one embodiment, blocking is measured as the displacement of labeled RgIA from the $\alpha 9\alpha 10$ subtype of the nAChR by a synthetic analgesic peptide disclosed herein. In one embodiment, blocking can be a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% displacement of labeled RgIA from the $\alpha 9\alpha 10$ subtype of the nAChR by a synthetic analgesic peptide disclosed herein.

In a second embodiment, activity can be measured by conducting a biological assay on a synthetic analgesic peptide disclosed herein to determine its therapeutic activity as compared to the results obtained from the biological assay of RgIA. In one embodiment, the effect can be 10-fold, 100-fold, 1000-fold, 2,000-fold, 3,000-fold, 4,000-fold, 5,000-fold, 6,000-fold, 7,000-fold, 8,000-fold, 9,000-fold, 10,000-fold, 20,000-fold, 30,000-fold, 40,000-fold, 50,000-fold, 60,000-fold, 70,000-fold, 80,000-fold, 90,000-fold, or 100,000-fold greater therapeutic activity of synthetic analgesic peptide disclosed herein when compared to RgIA as measured by the biological assay.

In a third embodiment, the binding affinity of a synthetic analgesic peptide disclosed herein to the $\alpha 9\alpha 10$ subtype of the nAChR can be measured and compared to the binding affinity of RgIA to the $\alpha 9\alpha 10$ subtype of the nAChR. In one embodiment, blocking can be a 10-fold, 100-fold, 1000-fold, 2,000-fold, 3,000-fold, 4,000-fold, 5,000-fold, 6,000-fold, 7,000-fold, 8,000-fold, 9,000-fold, 10,000-fold, 20,000-fold, 30,000-fold, 40,000-fold, 50,000-fold, 60,000-fold, 70,000-fold, 80,000-fold, 90,000-fold, or 100,000-fold greater binding affinity of the synthetic analgesic peptide disclosed herein over RgIA.

In a fourth embodiment, the effect of a synthetic analgesic peptide disclosed herein on the function of the $\alpha 9\alpha 10$ subtype of the nAChR is analyzed by measuring the effect in functional assays, such as electrophysiological assays, calcium imaging assays, and the like. In one embodiment, blocking includes a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% reduction in the function of the $\alpha 9\alpha 10$ subtype of the nAChR as measured by a functional assay when compared to RgIA.

Pharmaceutical compositions containing a compound of the present invention as the active ingredient can be prepared according to conventional pharmaceutical compounding techniques. See, for example, Remington: The Science and Practice of Pharmacy, 21st Ed., Lippincott Williams & Wilkins, Philadelphia, 2005. Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698, incorporated by reference herein.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer and Hatton (1993), Zimm et al. (1984) and Ettinger et al. (1978)); (b), microencapsulation (see, e.g., U.S. Pat. Nos. 4,352,883; 4,353,888; and 5,084,350, each of which is incorporated by reference herein); (c) continuous release polymer implants (see, e.g., U.S. Pat. No. 4,883,666); (d) macroencapsulation (see, e.g., U.S. Pat. Nos. 5,284,761, 5,158,881, 4,976,859 and 4,968,733 and published PCT patent applications WO92/19195, WO 95/05452, each of which is incorporated by reference herein); (e) naked or unencapsulated cell grafts to the CNS (see, e.g., U.S. Pat. Nos. 5,082,670 and 5,618,531, each of which is incorporated by reference herein); (f) injection, either subcutaneously, intravenously, intra-arterially, intramuscularly, or to other suitable site; or (g) oral administration, in capsule, liquid, tablet, pill, or prolonged release formulation, all of which are incorporated by reference herein.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Active agents, which may be peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635, each of which is incorporated by reference herein. Suitable DNA sequences can be prepared synthetically for each active agent on the basis of the developed sequences and the known genetic code.

The active agent is preferably administered in a therapeutically effective amount Dosage may be adjusted appropriately to achieve desired drug levels, locally or systemically. Typically, the active agents of the present invention exhibit their effect at a dosage range from about 0.001 mg/kg to about 250 mg/kg, preferably from about 0.01 mg/kg to about 100 mg/kg of the active ingredient, more preferably from about 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example, 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use on humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the active agents of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination with a supplementary potentiating agent. The individual drugs of the cocktail are each administered in therapeutically effective amounts. A therapeutically effective amount will be determined by the parameters described above; but, in any event, is that amount which establishes a level of the drugs in the area of the body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., Molecular Cloning (Cold Spring Harbor Laboratory Press, Cold Spring Harbor, N.Y., 1982); Sambrook et al., Molecular Cloning, 2nd Ed. (Cold Spring Harbor Laboratory Press, Cold Spring Harbor, N.Y., 1989); Sambrook and Russell, Molecular Cloning, 3rd Ed. (Cold Spring Harbor Laboratory Press, Cold Spring Harbor, N.Y., 2001); Ausubel et al., Current Protocols in Molecular Biology (John Wiley & Sons, updated through 2005); Glover, DNA Cloning (IRL Press, Oxford, 1985); Anand, Techniques for the Analysis of Complex Genomes, (Academic Press, New York, 1992); Guthrie and Fink, Guide to Yeast Genetics and Molecular Biology (Academic Press, New York, 1991); Harlow and Lane, Antibodies, (Cold Spring Harbor Laboratory Press, Cold Spring Harbor, N.Y., 1998); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, (Blackwell Scientific Publications, Oxford, 1988); Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebra fish (*Danio rerio*), 4th Ed., (Univ. of Oregon Press, Eugene, Oreg., 2000).

EXAMPLES

The present invention is described by reference to the following Examples, which are offered by way of illustration and are not intended to limit the invention in any manner. Standard techniques well known in the art or the techniques specifically described below were utilized.

Example 1: Testing Analogs

All penicillamine-containing RgIA analogues were synthesized following standard Fmoc protocols for solid phase peptide synthesis. Commercially available Fmoc-L-Pen (Trt)-OH or Fmoc-D-Pen(Trt)-OH amino acids were used for peptide synthesis. Orthogonal protection of the cysteine, which is well known in the art, was employed to sequentially form disulfide bridges between Pen-Cys, Cys-Cys or Pen-Pen. Peptides with either a single Pen substitution or di-Pen substitutions were tested. The activity of the peptides was determined by using cloned α9α10 nAChRs expressed in *Xenopus* oocytes. The assay measures a response to the neurotransmitter acetylcholine. The peptides block the response by binding to the same receptor, which prevents the acetylcholine from acting. Briefly, *Xenopus laevis* oocytes were used to express cloned human nAChR subtypes heterologously. Recordings were made 1-5 d post injection. Oocytes were voltage-clamped at −70 mV at room temperature and exposed to acetylcholine and conotoxin or synthetic analgesic peptides as described previously (McIntosh at al, et al. (2005) J Biol Chem 280(34):30107-30112.)

For the peptides of Table 1, the correct disulfide scaffold for the synthetic analgesic peptides is Cys2-Cys8, Cys3-Cys12. The synthetic analgesic peptides that were used and tested are shown in Table 1 along with the test results.

A peptide's ability to block the human α9α10 nAChR shall be understood to be synonymous with the peptide's activity for the human α9α10 nAChR. Thus, a peptide with a relatively high activity for the human α9α10 nAChR is able to block the human α9α10 nAChRs to a relatively high degree.

Replacement of either Cys2 or Cys8 with L-penicillamine produces analogs with greatly reduced activity for human α9α10 nAChRs indicating a crucial role of these two cysteines for the activity of this peptide. Substitution of cysteine 12 with L-penicillamine makes the RgIA4 analogs quickly reversible and having a 30-fold loss of potency ($IC_{50}$=32 nM). Notably, substitution of cysteine 3 with L-penicillamine leads to an analogue [C3Pen]RgIA4 with retained potency ($IC_{50}$=1.3 nM), and increased stability under basic conditions.

The most potent analog was [C3Pen;Y13bhY;14R]RgIA5 (SEQ ID NO: 37), which has cysteine 3 substituted with penacillamine and tyrosine 13 substituted with beta-homotyrosine. Beta-homotyrosine at residue 13 results in a peptide that is approximately 9-fold more potent than the same peptide with tyrosine at residue 13 (compare $IC_{50}$ values for [C3Pen;Y13bhY;14R]RgIA5 (SEQ ID NO:37) vs. [C3Pen; 14R]RgIA5 (SEQ ID NO: 41)).

TABLE 1

| Name | Sequence | $IC_{50}$ (nM) | 95% CI | Ave Resp. (Concen., nM) | SEM |
|---|---|---|---|---|---|
| [C2Pen]RgIA4 | G(Pen)CTDPRC(Cit)(I-3-Y)QCY (Seq ID No: 23) | 1109 | (620-2000) | | |
| [C3Pen]RgIA4 | GC(Pen)TDPRC(Cit)(I-3-Y)QCY (Seq ID No: 24) | 1.3 | (1.0-1.6) | | |
| [C8Pen]RgIA4 | GCCTDPR(Pen)(Cit)(I-3-Y)QCY (Seq ID No: 25) | >1000 | | 9.6% (1000) | 4.3 |
| [C12Pen]RgIA4 | GCCTDPRC(Cit)(I-3-Y)Q(Pen)Y (Seq ID No: 26) | 32 | (19-52) | | |
| [C2Pen;C8Pen]RgIA4 | G(Pen)CTDPR(Pen)(Cit)(I-3-Y)QCY (Seq ID No: 27) | >1000 | | 19% (1000) | 2.4 |
| [C3pen;C12Pen]RgIA4 | GC(Pen)TDPRC(Cit)(I-3-Y)Q(Pen)Y (Seq ID No: 28) | 29 | (15-56) | | |
| [C2d-Pen]RgIA4 | G(d-Pen)CTDPRC(Cit)(I-3-Y)QCY (Seq ID No: 29) | >100 | | 31% (100) | 11 |
| [C3d-Pen]RgIA4 | GC(d-Pen)TDPRC(Cit)(I-3-Y)QCY (Seq ID No: 30) | >1000 | | 34% (1000) | 3.9 |
| [C12d-Pen]RgIA4 | GCCTDPRC(Cit)(I-3-Y)Q(d-Pen)Y (Seq ID No: 31) | >100 | | 20% (100) | 1.2 |
| [C3Pen;Y13y]RgIA4 | GC(Pen)TDPRC(Cit)(I-3-Y)QCy (Seq ID No: 32) | 4.6 | (3.6-6) | | |
| [C3Pen;Y13y;14r]RgIA4 | GC(Pen)TDPRC(Cit)(I-3-Y)QCyr (Seq ID No: 33) | 6.3 | (4.6-8.6) | | |
| [C3Pen;l4R]RgIA4 | GC(Pen)TDPRC(Cit)(I-3-Y)QCYR (Seq ID No: 34) | 1.3 | (0.98-1.7) | | |
| [C3Pen;Y13bhY;14R]RgIA4 | GC(Pen)TDPRC(Cit)(I-3-Y)QC(bhY)R (Seq ID No: 35) | 0.43 | (0.16-1.2) | | |
| [C3Pen;Y13bhY;14r]RgIA4 | GC(Pen)TDPRC(Cit)(I-3-Y)QC(bhY)r (Seq ID No: 36) | 2.1 | (1.9-2.3) | | |
| [C3Pen;Y13bhY;14R]RgIA5 | GC(Pen)TDPRCR(I-3-Y)QC(bhY)R (Seq ID No: 37) | 0.055 | (0.036-0.084) | | |
| [C3Pen;Y13bhY;14r]RgIA5 | GC(Pen)TDPRCR(I-3-Y)QC(bhY)r (Seq ID No: 38) | 0.31 | 0.23-0.40 | | |
| [C3Pen;14R]RgIA5 | GC(Pen)TDPRCR(I-3-Y)QCYR (SEQ ID NO: 41) | 0.50 | 0.42-0.6 | | |

CI, confidence interval;
Ave Resp., average response at indicated concentration;
Concen., peptide concentration;
SEM, standard error of the mean;
bhY, beta-homotyrosine. Amino acids are given their standard one letter abbreviation. Lower case single letters indicate D-amino acids. d-Pen indicates D-penicillamine. Pen indicates L-penicillamine. Y13bhY indicates that the tyrosine in the 13$^{th}$ position is replaced by beta-homotyrosine. Y13y indicates that the tyrosine in the 13$^{th}$ position is replaced by D-tyrosine. 14R means an arginine is added to the peptide at position 14. 14r means a D-arginine is added to the peptide at position 14.

Other RgIA4 analogs which can block human α9α10 nAChRs comprise the sequences set forth in Table 2.

TABLE 2

| SEQUENCE | SEQ ID NO. |
|---|---|
| G X1 C T D P R C (Cit) (R-3-Y) Q C Y | 5 |
| G C X1 T D P R C (Cit) (R-3-Y) Q C Y | 6 |
| G C C T D P R X1 (Cit) (R-3-Y) Q C Y | 7 |
| G C C T D P R C (Cit) (R-3-Y) Q X1 Y | 8 |
| G X1 C T D P R X1 (Cit) (R-3-Y) Q C Y | 9 |
| G C X1 T D P R C (Cit) (R-3 -Y) Q X1 Y | 10 |
| G C X1 T D P R C (Cit) (R-3-Y) Q C X2 X3 | 11 |
| G X1 C T D P R C R (R-3-Y) Q C Y | 12 |
| G C X1 T D P R C R (R-3-Y) Q C Y | 13 |
| G C C T D P R X1 R (R-3-Y) Q C Y | 14 |
| G C C T D P R C R (R-3-Y) Q X1 Y | 15 |
| G X1 C T D P R X1 R (R-3-Y) Q C Y | 16 |
| G C X1 T D P R C R (R-3-Y) Q X1 Y | 17 |
| G C X1 T D P R C R (R-3-Y) Q C X2 X3 | 18 |
| X0 X1 X2 X3 T D P X4 C (Cit) X5 X6 C X7 | 19 |
| X0 X1 X2 X3 T D P X4 C X4 X5 X6 C X7 | 20 |
| X0 X1 X2 X3 T D P X4 C (Cit) X5 X6 C X7 X8 | 21 |
| X0 X1 X2 X3 T D P X4 C X4 X5 X6 C X7 X8 | 22 |

With respect to each of the foregoing sequences in the set of sequences having SEQ ID NO: 5 through SEQ ID NO: 18, the following selection conditions are applied independently across the set of sequences:

X1 in at least one occurrence thereof in such sequence, and up to and including all occurrences thereof in such sequence, is in each position independently selected from the group consisting of L-Penicillamine (L-Pen) and D-Penicillamine (D-Pen), and in all other occurrences thereof, if any, is L-Cysteine; X2 in such sequence is selected from the group consisting of L-Tyrosine and D-Tyrosine; X3 in such sequence is any amino acid; Cit is citrulline, and R-3-Y is 3-R-tyrosine.

With respect to each of the foregoing sequences in the set of sequences having SEQ ID NO: 19 through SEQ ID NO: 22, the following selection conditions are applied independently across the set of sequences:

X0 in such sequence is pyroglutamate or des-X0; X1 in such sequence is selected from the group consisting of L-Glycine, des-X1, and pyroglutamate; X2 in such sequence is selected from the group consisting of L-Cysteine, L-Penicillamine and D-Penicillamine; X3 in such sequence is selected from the group consisting of L-Penicillamine and D-Penicillamine; X4 in such sequence is, in each position, independently selected from the group consisting of the Third Group of Peptide Residues; X5 in such sequence is selected from the group consisting of the First Group of Peptide Residues; X6 in such sequence is selected from the group consisting of L-Glutamine, D-Glutamine, L-Asparagine, D-Asparagine, and the Third Group of Peptide Residues; X7 in such sequence is selected from the group consisting of L-Tyrosine, D-Tyrosine, a D-beta homo amino acid, an L-beta homo amino acid, the Second Group of Peptide Residues, and the Third Group of Peptide Residues; X8 in such sequence is selected from the group consisting of an L-amino acid, a D-amino acid, an L-beta homo amino acid, a D-beta homo amino acid, the Second Group of Peptide Residues, and the Third Group of Peptide Residues; Cit is citrulline; and in the synthetic analgesic peptide, the C-terminal amino acid is selected from the group consisting of amidated amino acids and non-amidated amino acids.

Example 2: Stability of RgIA4 Analogs

Experiments were performed to determine the stability of RgIA4 analogs of the invention. These experiments demonstrated that [C3Pen]RgIA4 analog (SEQ ID NO: 24) has markedly increased stability as compared to the unmodified RgIA4 peptide (SEQ ID NO: 39).

Peptide samples (50 nmol, 0.25 mM) were dissolved in a solution containing: 0.25 mM reduced glutathione, 100 mM phosphate buffer plus 1 mM EDTA, pH 7.3 (total volume: 200 µl), and incubated at 37° C. for various time intervals. Aliquots (25 µl) were taken at 1 min, 30 min, 1 h, 2 h, 4 h, 8 h, quenched with extraction buffer consisting of 50% aqueous acetonitrile, 100 mM NaCl, and 1% trifluoroacetic acid (25 µl), and analyzed by RP-HPLC.

The results of these experiments are presented in FIG. 1. At time points greater than or equal to 30 minutes, unmodified RgIA4 (SEQ ID NO: 39) is the minority component. In contrast, [C3Pen]RgIA4 is the majority product at all time points. At 8 h, the area under the curve for RgIA4 was 26.3% of the total. At 8 h, the area under the curve for RgIA4 [C2Pen] was 92.3% of the total. As demonstrated in FIG. 1, the C3Pen analog of RgIA4 remains in the preferred disulfide configuration (globular form) in the presence of reducing buffer. This is in contrast to the unmodified RgIA4 which quickly converts to the ribbon form.

These data demonstrate that [C3Pen]RgIA4 analog (SEQ ID NO: 24) is significantly more stable than the unmodified RgIA4 peptide (SEQ ID NO: 39).

Example 3: Penicillamine Substituted RgIA Analogs Exhibit Significantly Higher Activity as Compared to Selenocysteine Substituted Analogs The cysteine at position 2 is critical to the activity of the synthetic analgesic peptides of the invention. The present invention is based on the finding that the most potent synthetic analgesic peptides, have a penicillamine substitution for Cys3 and not Cys2, Cys8 or Cys12. This is surprising given the previous literature on selenocysteine.

Selenocysteine (Sec) is a naturally occurring amino acid with a structure similar to cysteine, but with selenium taking the place of sulfur. Penicillamine (Pen) is a beta dimethyl analog of cysteine. It has been demonstrated previously that Sec-Sec (diselenide bond) replacement of Cys-Cys (disulfide bond) in synthetic analgesic peptides results in analogs with potency equal to or slightly greater to that of the native peptide.

Briefly, the following assays were conducted by testing the peptides on nAChRs heterologously expressed in *Xenopus* oocytes. Peptides were tested for their ability to block the response to acetylcholine. Peptide concentration-response curves were generated to determine the concentration at which 50% of the acetylcholine response was blocked ($IC_{50}$).

Sec substituted forms of the α-conotoxin analog identified as α-conotoxin ImI have approximately equal potency for blocking α7 nAChR (See C. J. Armishaw, N. L. Daly, S. T. Nevin, D. J. Adams, D. J. Craik, and P. F. Alewood, Alpha-selenoconotoxins, a new class of potent alpha7 neuronal nicotinic receptor antagonists, J Biol Chem 281 (2006) 14136-43).

TABLE 3

| Peptide Name | $IC_{50}$ |
| --- | --- |
| α-conotoxin ImI | 69.3 ± 15.5 nM |
| [C2Sec;C8Sec] ImI | 49.5 ± 16.2 nM |
| [C3Sec ;C12Sec] ImI | 50.3 ± 8.4 nM |

The [C2Sec,C8Sec] AuIB analog has higher potency than the [C3Sec;C15Sec] AuIB analog for blocking the α3β4 nAChR (See M. Muttenthaler, S. T. Nevin, A. A. Grishin, S. T. Ngo, P. T. Choy, N. L. Daly, S. H. Hu, C. J. Armishaw, C. I. Wang, R. J. Lewis, J. L. Martin, P. G. Noakes, D. J. Craik, D. J. Adams, and P. F. Alewood, Solving the alpha-conotoxin folding problem: efficient selenium-directed on-resin generation of more potent and stable nicotinic acetylcholine receptor antagonists. J Am Chem Soc 132 (2010) 3514-22).

TABLE 4

| Peptide Name | $IC_{50}$ |
| --- | --- |
| α-conotoxin AuIB | 3100 ± 1002 nM |
| [C2Sec;C8Sec] AuIB | 260 ± 20 nM |
| [C3 Sec;C15 Sec] AuIB | 1000 ± 359 nM |

Sec substituted forms of the α-conotoxin analog identified as RgIA have high potency for blocking the rat α9α10 nAChR, again indicating that Sec may be favorably substituted into all Cys positions.

TABLE 5

| Peptide Name | $IC_{50}$ |
| --- | --- |
| α-conotoxin RgIA | 5.2 nM (See Vincler et al., 2006, Proc Natl Acad Sci U S A 103 (2006) 17880-4) |
| [C2Sec;C8Sec] RgIA | <10 nM (96.9 ± 1.4% block at 10 nM) |
| [C3 Sec;C12Sec] RgIA | <10 nM (81.9 ± 1.8% block at 10 nM) |

The literature suggests that Sec analog substitution for any Cys would be favorable. Further it suggests that substitution for Cys2 or Cys8 might be most favorable. However, the present data indicate that the activity of a Pen substituted analog cannot be predicted from data obtained for Sec substituted analogs. In fact, substitution of penicillimine for Cys2 or Cys8 severely compromises activity.

Experiments were performed to determine the activity of RgIA4 analogs having single or double Pen substitutions. The resulting data provides a pattern of activity for Pen-substituted analogs that is significantly different from that which was previously demonstrated for Sec substituted analogs. Notably, certain Pen substituted RgIA4 analogs are substantially more active than any on the Sec substituted analogs. The increased activity of the Pen substituted RgIA4 analogs could not be predicted based on the level of activity of the various Sec substituted analogs. The Pen substituted RgIA4 analogs with enhanced activity offer numerous advantages, in particular, administration at lower dosages, which would correlate with decreased off target effects and decreased toxicity.

There are substantial differences in the effects of Pen substitution for Cys in RgIA4 analogs with respect to blocking the human α9α10 nAChR as compared to Sec substitution for Cys as presented in the table below. The activity of RgIA4 presented in the table below is provided in H. K. Romero, S. B. Christensen, L. Di Cesare Mannelli, J. Gajewiak, R. Ramachandra, K. S. Elmslie, D. E. Vetter, C. Ghelardini, S. P. Iadonato, J. L. Mercado, B. M. Olivera, and J. M. McIntosh, Inhibition of alpha9alpha10 nicotinic acetylcholine receptors prevents chemotherapy-induced neuropathic pain. Proc Natl Acad Sci USA 114 (2017) E1825-E1832.

TABLE 6

| Peptide Name | Sequence | IC$_{50}$ |
| --- | --- | --- |
| RgIA4 | GCCTDPRC(Cit)(I-3-Y)QCY (SEQ ID NO: 39) | 1.5 ± 0.5 nM |
| [C2Pen;C8Pen] RgIA4 | G(Pen)CTDPR(Pen)(Cit)(I-3-Y)QCY (SEQ ID NO: 27) | >1000 nM (19 ± 2.4% block at 1000 nM) |
| [C3Pen;C12Pen] RgIA4 | GC(Pen)TDPRC(Cit)(I-3-Y)Q(Pen)Y (SEQ ID NO: 28) | >33 nm |
| [C2Pen]RgIA4 | G(Pen)CTDPRC(Cit)(I-3-Y)QCY (SEQ ID NO: 23) | 1109 nM |
| [C3Pen]RgIA4 | GC(Pen)TDPRC(Cit)(I-3-Y)QCY (SEQ ID NO: 24) | 1.3 nM |
| [C8Pen]RgIA4 | GCCTDPR(Pen)(Cit)(1-3-Y)QCY (SEQ ID NO: 25) | >1000 nM (9.6 ± 4.3% response at 1000 nM) |

Substitution of Pen-Pen for Cys-Cys results in much lower activity for human α9α10 nAChR. Surprisingly, the activity of various Pen substituted RgIA analogs is quite different from that of Sec substituted RgIA analogs. The high level of activity of [Cys3Pen]RgIA4 makes it an ideal candidate for therapeutic use in the treatment of pain.

There are additional advantages to using a Pen substituted analog rather than a Sec substituted analog. The cost of producing a penicillamine substituted peptide is much less than that of producing a selenocysteine substituted peptide. Selenocysteine is significantly more expensive than penicillamine. For example, the solid phase synthesis reagent Fmoc-(S)-4-methoxybenzyl selenocysteine has a list price of $2590/gram (Chem-Impex, Wood Dale, Ill.) vs. $130/gram for Fmoc-S-trityl-L-penicillamine (Chem-Impex, Wood Dale, Ill.).

More significantly, penicillamine use avoids potential selenium toxicity associated with selenocysteine. Selenium is an essential trace element. However, exceeding recommended intakes can cause selenosis, with signs that include hair loss, fatigue, irritability and nervous system abnormalities. (See Dietary Reference Intakes for Vitamin C, Vitamin E, Selenium, and Carotenoids, ISBN 978-0-309-06949-6 DOI 10.17226/9810, Panel on Dietary Antioxidants and Related Compounds, Subcommittees on Upper Reference Levels of Nutrients and Interpretation and Uses of DRIs, Standing Committee on the Scientific Evaluation of Dietary Reference Intakes, Food and Nutrition Board, Institute of Medicine).

Example 4: Cys3 Penicillamine Substituted RgIA Analogs Exhibit Significantly Higher Activity as Compared to Dicarba Substituted Analogs Dicarba-cystino substitution of disulfide bonds may be used to prevent disulfide scrambling. Dicarba analogs of RgIA were synthesized by Chhabra et al. The resulting analogs were substantially less potent at blocking the α9α10 nicotinic acetylcholine receptor than the native peptide. The IC$_{50}$ of the analogs ranged from 1150-36,000 nM compared to 8.2 nM for native RgIA. Thus, there is a 140 to >3600-fold reduction in potency. In contrast, substitution of penicillamine for Cys3 of RgIA4 produced an analog that retains high potency (1.3 nM). As demonstrated above, one analog, [C3Pen;Y13bhY;14R]RgIA5 (SEQ ID NO: 37), has an IC$_{50}$ of 0.055 nM. Thus the penicillamine analogs of the invention wherein cysteine 3 is substituted with penicillamine, and where tyrosine 13 is substituted with beta-homotyrosine, have high activity, with the most potent penicillamine analog being ~20,000-fold more potent than the most potent reported dicarba analog (0.055 nM vs. 1150 nM) (See Chhabra et al., supra).

Example 5: SEQ ID NO: 37 Alleviates Oxaliplatin-Induced Cold Allodynia in Mice

Oxaliplatin is an anticancer drug used in chemotherapy treatments of certain colorectal, ovarian, and pancreatic cancers. A severe complication accompanying the use of this drug is the development neuropathic pain, which affects most colorectal cancer patients. Two-thirds of patients will have symptoms that last longer than 12 months. Persistent peripheral neuropathy was observed in 60% of patients two years after the final treatment (Andre et al., 2004, Briani et al., 2014, Park et al., 2013, Seretny et al., 2014).

Briefly, mice were injected once per day with oxaliplatin (3.5 mg/kg i.p) or 0.9% saline (vehicle). In addition, mice were injected once per day s.c. with the peptide (4 µg/kg) consisting of SEQ ID NO: 37 or vehicle. During the treatment period, mice were injected once per day, 5 days per week for 3 weeks (shown by solid bars in FIG. 2). Twenty-four hours after last injection, mice were assessed for cold allodynia using a cold-plate temperature ramp protocol as described (Romero et al., 2017). The injection schedule was repeated for two additional weeks. Treatments were stopped on day 21; cold-plate assessment was performed 24 h later on day 22; subsequent tests were performed once a week. Time to respond to decreasing temperature was measured and indicated on the y-axis (mean SEM). Data was analyzed using a one-way ANOVA with Dunnett's Multiple Comparison Test. Experimenters were blinded to the identity of the injected compounds.

Figure 2:
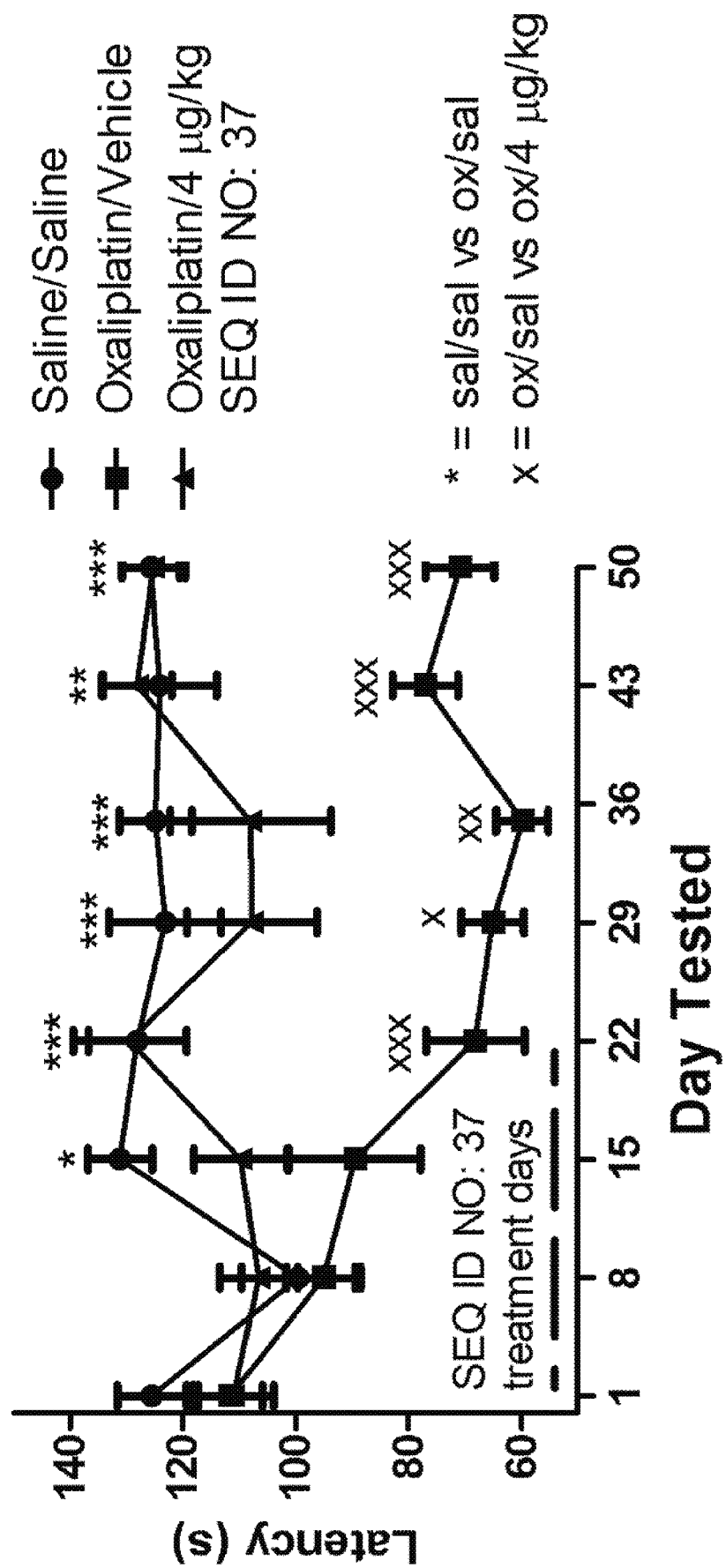
FIG. 2 shows the effects of a peptide consisting of SEQ ID NO: 37 on oxaliplatin-induced cold allodynia in mice. The effects of the peptide consisting of SEQ ID NO: 37 persisted for an additional 4 weeks after treatment was stopped, consistent with a disease modifying effect. Treatment days (total of 15) are indicated by line. x or * indicates $P<0.05$; xx or  indicates $P<0.01$; and xxx or * indicates $P<0.001$. Saline (sal); oxaliplatin (ox). n=8 for each experimental group.

As shown in FIG. 2, mice administered oxaliplatin show evidence of peripheral neuropathy indicated by hypersensitivity to non-noxious cold (square symbols) compared to saline only injected control mice (circle symbols). Administration of the peptide consisting of SEQ ID NO: 37 alleviated the oxaliplatin induced hypersensitivity demonstrating its in vivo efficacy (triangle symbols). The effects of peptide administration persisted for 4 weeks after discontinuation of peptide administration, consistent with a disease modifying effect.

Example 6: RgIA Analogs Relieve Chemotherapy-Induced Neuropathic Pain

Oxaliplatin is a first-line chemotherapeutic agent used to treat colorectal cancers. In humans, side effects include neurotoxicity, and prominent symptoms of acute neuropathy include sensitivity to touching cold items, discomfort in swallowing cold items, throat discomfort, and muscle cramps. Cold-related sensitivity is rated as the most severe symptom. Oxaliplatin-induced peripheral neuropathic pain in rats is a commonly used model of human chemotherapy-induced neuropathic pain (26). Oxaliplatin-Induced Neuropathic Pain in Rats. Neuropathy in rats (Harlan) is induced as described by Cavaletti et al. (54). Briefly, rats are treated with 2.4 mg/kg i.p. oxaliplatin (Sequoia Research Products) for 5 consecutive days every week for 3 weeks (15 i.p. injections). Throughout the study period, experimenters are blinded as to the identity of the injected compounds. Data is analyzed with one-way ANOVA using Dunnett's multiple comparison test (GraphPad Prism). Rat Cold Plate Test. As previously described (55), rats are placed in a stainless steel box (12 cm×20 cm×10 cm) with a cold plate as the floor. The temperature of the cold plate is kept constant at 4+1° C. Pain-related behaviors (i.e., lifting and licking of the hind paw) are observed, and the time of the first sign are recorded. The cutoff time of the latency of paw lifting or licking is set at 60 s.

The pain-relieving effects of RgIA analog on chemotherapy-induced neuropathic pain is determined. Oxaliplatin administration in rats produces cold allodynia (i.e., pain due to a cold stimulus that does not usually provoke pain). Repeated daily s.c. injections (5 d each week) of RgIA analogs at doses of 0.128-80 µg/kg were administered and chemotherapy-induced cold allodynia assessments were performed 24 h after the last RgIA analog dose on days 8, 15, and 22. Repeated oxaliplatin administration in rats also induces a low pain threshold in response to mechanical noxious stimuli. The effects of administration of RgIA analogs (0.128-80 µg/kg) on mechanical hypersensitivity at 30 min and 24 h post-RgIA analog dosing are determined, for example by a Randall-Selitto test.

Rat Paw Pressure Test. The nociceptive threshold in the rat is determined with an analgesimeter (Ugo Basile) as previously described (56). Briefly, a constantly increasing pressure is applied to a small area of the dorsal surface of the hind paw using a blunt conical probe. Mechanical pressure is increased until vocalization or a withdrawal reflex occurs. Vocalization or withdrawal reflex thresholds are expressed in grams. For analgesia measures, mechanical pressure application is stopped at 120 g.

The effects of RgI analogs on Oxaliplatin-Induced Neuropathic Pain is also evaluated in mice. For these studies, oxaliplatin (MedChem Express) is dissolved at 0.6 µg/µL in 0.9% NaCl. RgIA4 is dissolved at 0.01 µg/µL in 0.9% NaCl. For each experiment, mice are divided into four equally sized groups (n=7-9 animals) and injected with saline (i.p.)+saline (s.c.), saline (i.p.)+RgIA4 (40 µg/kg, s.c.), oxaliplatin (2.4 mg/kg i.p.)+saline (s.c.), or oxaliplatin (2.4 mg/kg, i.p.)+RgIA4 (40 µg/kg, s.c.). In the first study, mice are injected once per day on Wednesday, Thursday, and Friday, and again on Monday and Tuesday. On Wednesday, mice are tested before injection (24-h time point) and 30 min after injection. This pattern is repeated for an additional 2 wk. In a second set of experiments, mice are injected once per day on Monday through Friday and tested on Monday before injection (72-h time point). This pattern is repeated for an additional 2 wk.

For mice, testing is conducted using a cold-plate test chamber (IITC, Inc. Life Science). Animals are allowed to acclimate in the chamber at room temperature (23° C.) for 5 min. Temperature is then lowered at a rate of 10° C. per minute. The testing is stopped when the animal lifts both forepaws and shaking or licking occurs. Alternating lifting of forepaws is not scored.

Throughout the study period, experimenters are blinded as to the identity of the injected compounds. Data are analyzed with one-way ANOVA using Dunnett's multiple comparison test (GraphPad Prism).

Oxaliplatin is a first-line chemotherapeutic agent used to treat colorectal cancers. In humans, side effects include neurotoxicity, and prominent symptoms of acute neuropathy include sensitivity to touching cold items, discomfort in swallowing cold items, throat discomfort, and muscle cramps. Cold-related sensitivity is rated as the most severe symptom. Oxaliplatin-induced peripheral neuropathic pain in rats is a commonly used model of human chemotherapy-induced neuropathic pain (26). For example, chemotherapy-induced neuropathic pain is induced via intravenous injection of oxaliplatin (2.4 mg/kg) twice a week for 3 weeks. The pain-relieving effects of RgIA analog on chemotherapy-induced neuropathic pain are determined. Oxaliplatin administration in rats produces cold allodynia (i.e., pain due to a cold stimulus that does not usually provoke pain). Repeated daily s.c. injections (5 d each week) of RgIA analogs at doses of 0.128-80 µg/kg were administered and chemotherapy-induced cold allodynia assessments were performed 24 h after the last RgIA analog dose on days 8, 15, and 22 to determine if the RgIA analogs reduced pain. Repeated oxaliplatin administration in rats also induces a low pain threshold in response to mechanical noxious stimuli. The effects of administration of RgIA analogs (0.128-80 µg/kg) on mechanical hypersensitivity at 30 min and 24 h post-RgIA analog dosing are determined, for example by a Randall-Selitto test.

Example 7: RgIA Analogs Relieve Diabetic Peripheral Neuropathic Pain

The pain-relieving effects of RgIA analog on diabetic peripheral neuropathic pain is determined using the streptozatocin mouse model of diabetic neuropathy (Sullivan et al. 2007, Neurobiol Dis. December; 28(3): 276-85).

Testing is conducted using a hot-plate test chamber (IITC, Inc. Life Science). Animals were allowed to acclimate in the chamber at room temperature (23° C.) for 5 min. The temperature is then raised at a rate of 10° C. per minute. The testing is stopped when the animal lifts both forepaws and shaking or licking of the forepaws occurs, or when they lift either hind paw and shaking or licking of the hindpaw occurs. Alternating lifting of forepaws is not scored.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A synthetic analgesic peptide comprising the amino acid sequence:

G (Pen) C T D P R C (Cit) (I-3-Y) Q C Y (SEQ ID NO: 23);

G C (Pen) T D P R C (Cit) (I-3-Y) Q C Y (SEQ ID NO: 24);

G C C T D P R (Pen) (Cit) (I-3-Y) Q C Y (SEQ ID NO: 25);

G C C T D P R C (Cit) (I-3-Y) Q (Pen) Y (SEQ ID NO: 26);

G (Pen) C T D P R (Pen) (Cit) (I-3-Y) Q C Y (SEQ ID NO: 27);

G C (Pen) T D P R C (Cit) (I-3-Y) Q (Pen) Y (SEQ ID NO: 28);

G (D-Pen) C T D P R C (Cit) (I-3-Y) Q C Y (SEQ ID NO: 29);

G C (D-Pen) T D P R C (Cit) (I-3-Y) Q C Y (SEQ ID NO: 30);

G C C T D P R C (Cit) (I-3-Y) Q (D-Pen) Y (SEQ ID NO: 31);

G C (Pen) T D P R C (Cit) (I-3-Y) Q C D-Y (SEQ ID NO: 32);

G C (Pen) T D P R C (Cit) (I-3-Y) Q C D-Y D-R (SEQ ID NO: 33);

G C (Pen) T D P R C (Cit) (I-3-Y) Q C Y R (SEQ ID NO: 34); or

GC (Pen) T D P R C (Cit) (I-3-Y) Q C (bhY) D-R (SEQ ID NO: 35).

2. The synthetic analgesic peptide of claim 1, wherein the C-terminal amino acid is amidated.

* * * * *